US006187756B1

(12) United States Patent
Lee et al.

(10) Patent No.: US 6,187,756 B1
(45) Date of Patent: Feb. 13, 2001

(54) COMPOSITION AND METHODS FOR TREATMENT OF NEUROLOGICAL DISORDERS AND NEURODEGENERATIVE DISEASES

(75) Inventors: Robert K. K. Lee; Richard J. Wurtman, both of Boston, MA (US)

(73) Assignee: The Massachusetts Institute of Technology, Cambridge, MA (US)

( * ) Notice: Under 35 U.S.C. 154(b), the term of this patent shall be extended for 0 days.

(21) Appl. No.: 09/493,228

(22) Filed: Jan. 28, 2000

Related U.S. Application Data

(62) Division of application No. 08/924,505, filed on Sep. 5, 1997, now Pat. No. 6,043,224.

(60) Provisional application No. 60/025,507, filed on Sep. 5, 1996, and provisional application No. 60/033,765, filed on Jan. 15, 1997.

(51) Int. Cl.[7] .............................................. A61K 31/70

(52) U.S. Cl. ........................... 514/26; 514/169; 514/182; 514/573; 514/878; 514/879

(58) Field of Search ............................ 514/26, 182, 169, 514/573, 879, 878

(56) References Cited

U.S. PATENT DOCUMENTS

| | | |
|---|---|---|
| 4,791,099 | 12/1988 | Aroonsakul . |
| 5,242,932 | 9/1993 | Gandy et al. . |
| 5,348,963 | 9/1994 | Gandy et al. . |
| 5,614,649 | 3/1997 | Iqbal et al. . |

OTHER PUBLICATIONS

Birge, J., *Am. Geriatric. Soc.*, 44, 865, (1996).
McCarthy, et al., *J. Cell Biol.*, 85, 890 (1980).
Peganini, et al., *Am J. Epidemiol*, 140, 256 (1994).
Mills, et al., *J. Neurchem.*, 67, 1511 (1996).
Jaffe et al., *J. Biol. Chem.*, 269, 13065 (1994).
LeBlanc, *J. Neurochem.*, 1183 (1997).
Cordell, *Annu. Rev. Pharmacol. Toxicol.*, 34, 69 (1994).
LeBlanc, *J. Neurochem.*, 2300, (1996).
Selkoe, *Annu. Rev. Neurosci.*, 17, 489 (1994).
Lanrange, et al., *Soc. Neursci.Abstr.*, 22, 378, (1996).
Nitsch, et al., *Science*, 258, 304 (1992).
Henderson, et al., *Arch Neurol*, 51, 896 (1994).
Wolf, et al., *J. Biol. Chem.*, 270, 4916 (1995).
Thomlinson, (1992): In Greenfield's neuropathology (Adams, J.H. and Duchen L.W. eds.) pp. 1284–1410 Oxford University Press.
Caporaso, et al., *Proc. Nat'l. Acad.Sci. U.S.A.*, 89, 3055 (1992).
Buxbaum, et al., *Proc. Natl. Acad. Sci. U.S.A..*, 91, 4489 (1994).
Lee, et al., *J. Neurochem.* (*supp*), 69, S103B (1997).
Lee et al., *Proc. Natl. Acad. Sci. U.S.A.*, 92, 8083 (1995).
Lee, et al., *Proc. Nat'l. Acad. Sci. U.S.A..*, 94, 5422 (1997).
Ulus and Wurtman, *J. Pharm. Exp. Ther.*, 281, 149 (1997).
Buxbaum, et al., *Proc. Nat'l. Acad. Sci. U.S.A.*, 89, 10075 (1992).
Rich, et al. *Neurology*, 45, 51 (1995).
Anderson, et al., *Neurology*, 45, 1441 (1995).
McGeer, et al., *Lancet*, 335, 1037 (1990).
Nordstedt, et al., *Proc. Natl. Acad. Sci. U.S.A.*, 88, 8910 (1991).
Anderson, et al., *EMBO J.*, 8, 3627 (1989).
Neve, et al., *Neuron*, 1, 669 (1990).
Golde, et al., *Neuron*, 4, 253 (1990).
Lindsay, et al., *Neurology*, 44, 2073 (1994).
Moran, et al., *Proc. Natl. Acad. Sci. U.S.A.*, 92, 5341 (1995).
Rodgers, et al., *Neurology*, 43 1609 (1993).
Hsiao, et al., *Neuron*, 15, 1203–1218 (1995).
Siman, et al., *J.Neuron.*, 3, 275 (1989).
Maruyama, et al., *Nature*, 347, 566 (1990).
Banati, et al., *Cereb. Blood Flow Metab.*, 15, 647 (1995).
Kozlowski, et al., *J. Neurosci*, 12, 1679 (1992).
Brun, et al., *Neuodegeneration*, 4, 171 (1995).
Yanker, et al., *Science*, 245, 417 (1989).
Eftimiopoulos, et al., *J. Neurochem.*, 67, 872 (1996).
Caporaso, et al., *Proc. Nat'l Acad. Sci. U.S.A.*, 89, 2225 (1992).
Lee, et al., *J. Neurochem.*, 68, 1830 (1997).

*Primary Examiner*—James H. Reamer
(74) *Attorney, Agent, or Firm*—Gilberto M. Villacorta; Pepper Hamilton, LLP

(57) ABSTRACT

It has been discovered that the stimulation of β-adrenergic receptors, which activate cAMP formation, give rise to increased APP and GFAP synthesis in astrocytes. Hence, the in vitro or in vivo exposure of neuronal cells to certain compositions comprising β-adrenergic receptor ligands or agonists, including, e.g., norepinephrine, isoproterenol and the like, increases APP mRNA transcription and consequent APP overproduction. These increases are blocked by β-adrenergic receptor antagonists, such as propranolol. The in vitro or in vivo treatment of these cells with 8Br-cAMP, prostaglandin $E_2$ (PG $E_2$), forskolin, and nicotine ditartrate also increased APP synthesis, including an increase in mRNA and holoprotein levels, as well as an increase in the expression of glial fibrillary acidic protein (GFAP). Compositions and methods are disclosed of regulating APP overexpression and mediating reactive astrogliosis through cAMP signaling or the activation of β-adrenergic receptors. It has further been found that the increase in APP synthesis caused by 8Br-cAMP, PG $E_2$, forskolin, or nicotine ditartrate is inhibited by immunosuppressants or anti-inflammatory agents, such as cyclosporin A, and FK-506 (tacrolimus), as well as ion-channel modulators, including ion chelating agents such as EGTA, or calcium/calmodulin kinase inhibitors, such as KN93. The present invention has broad implications in the alleviation, treatment, or prevention of neurological disorders and neurodegenerative diseases, including Alzheimer's Disease.

19 Claims, 27 Drawing Sheets

APPs

Control PMA DNF

APP Holoprotein

Control PMA DNF

APP Holoprotein

COMPOSITION AND METHODS FOR TREATMENT OF NEUROLOGICAL DISORDERS AND NEURODEGENERATIVE DISEASES

RELATED APPLICATIONS

This application is a divisional application of U.S. application Ser. No. 08/924,505 filed Sep. 5, 1997, now U.S. Pat. No. 6,043,224 which claims priority to U.S. Provisional Application Ser. No. 60/025,507, filed Sep. 5, 1996, and U.S. Provisional Application Ser. No. 60/033,765, filed Jan. 15, 1997, each of which is herein incorporated by reference.

STATEMENT OF FEDERAL SUPPORT

The present invention is made in whole or in part with financial support from the Federal Government under grant NIH #MH-28783. The Federal Government may have rights in the invention.

1. FIELD OF THE INVENTION

The present invention relates to compositions and methods for the treatment of various neurological diseases and neurodegenerative disorders, particularly those affected by an overabundance of Amyloid Precursor Protein (APP). In particular, it has been discovered that APP synthesis is stimulated by activation of cell surface receptors coupled to the formation of cyclic adenosine monophosphate (cAMP) Moreover, it has been found that certain substances can inhibit APP synthesis, either directly or by antagonizing receptors coupled to cAMP formation.

2. BACKGROUND OF THE INVENTION

Alzheimer's Disease (AD) is the most common neurodegenerative disorder of aging, and is characterized by progressive dementia and personality dysfunction. The abnormal accumulation of amyloid plaques in the vicinity of degenerating neurons and reactive astrocytes is a pathological characteristic of AD.

As the fourth leading cause of death in industrialized societies, surpassed only by heart disease, stroke and cancer, AD affects 5–11% of the population over the age of 65 and 30% of those over the age of 85. The estimated cost of caring for the approximate 2.5–4.0 million AD cases in the USA exceeded $60 billion in 1991 alone. Considering the estimated 17–25 million existing AD cases worldwide, AD will no doubt become an escalating healthcare problem of unparalleled proportions as the world's geriatric population grows. Much work remains in the quest to find an effective treatment for AD.

APP processing is regulated by neurotransmitters and synaptic activity. Amyloid plaques in AD accumulate near dystrophic neurons and reactive astrocytes. B. Cordell, *Annu. Rev. Pharmacol. Toxicol.* 34, 69 (1994); D. J. Selkoe, *Annu. Rev. Neurosci.* 17, 489 (1994). The activation of neurotransmitter receptors, which are coupled to phosphotidylinositol (PI) hydrolysis or to protein kinase C (PKC) activation, can promote APP metabolism and decrease amyloid formation. R. M. Nitsch, B. E. Slack, R. J. Wurtman, J. H. Growdon, *Science* 258, 304 (1992); B. A. Wolf et al., *J. Biol. Chem.* 270, 4916 (1995); J. D. Buxbaum, A. A. Ruefli, C. A. Parker, A. M. Cypess, P. Greengard, *Proc. Natl. Acad. Sci. U.S.A.* 91, 4489 (1994); R. K. K. Lee, R. J. Wurtman, A. J. Cox, R. M. Nitsch, *Ibid.,* 92, 8083 (1995); Ulus and Wurtman, *J.Pharm.Exp.Ther.,* 281,149 (1997); Lee et al., *PNAS USA,* 92, 8083 (1995). Activation of neurotransmitters coupled to cAMP production suppresses both constitutive and PKC/PI-stimulated APPs secretion in astroglioma cells and in primary astrocytes. Eftimiopoulos et al., *J.Neurochem.,* 67, 872 (1996); Lee et al., *J.Neurochem.,* 68,1830 (1997). The inhibitory effect of cAMP on APPs secretion may be specific for astrocytic cells in that cAMP and PKA activation reportedly stimulate APPs secretion in pheochromocytoma PC-12 and human embryonic kidney cells. Xu et al., *PNAS USA,* 93, 4081 (1996); Marambaud et al., *J.Neurochem.,* 67, 2616 (1996). The drastic alterations in neurotransmitter levels and second messenger signalling created by neurodegeneration and synapse loss in AD may disrupt APP processing in ways that promote the accumulation of amyloidogenic or neurotoxic APP fragments. In contrast, the loss of various neurotransmitters in AD may increase cellular levels of APP holoprotein containing amyloidogenic or neurotoxic peptides due to a decrease in proper APP metabolism. B. A. Yankner et al., *Science,* 245, 417 (1989); M. R. Kozlowski, A. Spanoyannnis, S. P. Manly, S. A. Fidel, R. L. Neve, *J. Neurosci.* 12, 1679 (1992).

Increased APP production in Down's syndrome/Trisomy 21 is associated with a high incidence of AD at an early age due to the extra copy of the APP gene. Overexpression of APP in cell cultures and in transgenic mice is also associated with neurodegeneration and with age-related cognitive deficits, suggesting that overexpression of APP could contribute to the neuropathology of AD. K. Maruyama, K. Terakado, M. Usami, K. Yoshikawa, *Nature,* 347, 566 (1990); K. K. Hsiao et al., *Neuron* 15, 1203–1218 (1995); P. M. Moran, L. S. Higgins, B. Cordell, P. C. Moser, *Proc. Natl. Acad. Sci. U.S.A.* 92, 5341 (1995).

Several APP isoforms, ranging in size from 695–770 amino acids, are derived by differential splicing of a primary transcript. Of the three major APP isoforms, APP695 is predominantly expressed in neurons; APP751 and APP770, which harbor an additional Kunitz-type protease inhibitor (KPI) insert at the N-terminus, are predominantly expressed in astrocytes and appear to be increased in AD brain. T. E. Golde, S. Estes, M. Usiak, L. H. Younkin, S. G. Younkin, *Neuron* 4, 253 (1990); R. L. Neve, E. A. Finch, L. R. Dawes, *Ibid.,* 1, 669 (1990); J. P. Anderson et al., *EMBO J.* 8, 3627 (1989); C. Nordstedt et al., *Proc. Natl. Acad. Sci. U.S.A.* 88, 8910 (1991). The decreased amounts of APP695 in postmortem AD brains may be due to neuronal loss. The increase in KPI-containing APP isoforms in AD and in regions surrounding senile plaques raises the possibility that transcriptional activation of APP synthesis in astrocytes contributes to AD neuropathology.

2.1. Prior AD Studies

Aging, neurodegeneration and synapse loss in AD are associated with astrocyte proliferation and an upregulation of KPI-containing APP isoforms. See, e.g., A. Brun, X. Liu, C. Erikson, *Neurodegeneration* 4, 171 (1995); R. Schechter, S. H. C. Yen, R. D. Terry, *J. Neuropathol. Exp. Neurol.* 40, 95 (1981); L. A. Hansen, D. N. Armstrong, R. D. Terry, *Neurobiol. Aging* 8, 1 (1987); K. Iverfeldt, S. I. Walaas, P. Greengard, *Proc. Natl. Acad. Sci. U.S.A.* 90, 4146 (1993).

McGeer, P. L. et al., in *The Lancet,* 335, 1037 (1990), present the results of a retrospective study that revealed an apparently low incidence of Alzheimer's Disease in rheumatoid arthritis patients. These authors propose the possibility that anti-inflammatory therapy confers some protection against AD. While provocative, the authors' proposal is based solely on circumstantial evidence. This fact is not lost on the authors, who note three alternative explanations for their observations, in addition to the possible protective role of anti-inflammatory therapy.

Andersen, K. et al., in *Neurology* (August 1995) 45:1441, describe the results of their retrospective study. This article, perhaps, illustrates the care that one should take in conducting studies "in hindsight" because of the danger of over-interpretation or over-manipulation of the data in an effort to enhance any perceived differences. To their credit, the authors tempered their conclusions, stating that their findings are "compatible" with a possible protecting effect of NSAIDs (non-steroidal anti-inflammatory drugs) on the risk of AD. The authors fairly point out that important issues remain, including whether the presence of complement leads to neurodegeneration or whether the activation of complement is brought about by the cell's need to phagocytose damaged neurons, how long one has to be exposed to NSAIDs to obtain clinically detectable results, and the need for studies that are better designed. The article adds that no relationship between NSAIDs exposure and cognitive function is found.

In contrast, an earlier article by Rich, J. B. et al., which appeared in *Neurology* (January 1995) 45:51, reported on the results of their review of the records of 210 Alzheimer's patients. These authors concluded that patients on NSAIDs performed better on certain tests, including Mini-Mental State Examination, Boston Naming Test, delayed Benton Visual Retention Test, among others, versus non-NSAID patients. However, no significant difference is found in an even greater number of other tests performed, including Block Design, Immediate Benton Visual Retention Test, Gollin Incomplete Figures Test, to name a few. Recognizing the inherent limitations of their study, the authors state that "[m]ethodologic limitations inherent in retrospective studies such as this one preclude us from addressing the specificity of the protective effects of NSAIDs." Indeed, the patients examined are likely to be on several types of medication at once.

In fact, in an earlier study by Lindsay, J. and co-workers reported in *Neurology* (November 1994) 44:2073, it is found that those with arthritis had a significantly reduced risk of Alzheimer's disease. It is also found that the use of NSAIDs gave rise statistically to a lower risk. However, it is suggested that the presence of arthritis itself is the determinant in lowering the apparent risk for developing Alzheimer's disease and not the taking of NSAIDs.

One has to go back even earlier to a study by Rogers, J. et al., in *Neurology* (August 1993) 43:1609, to find a controlled 6-month investigation involving the administration of 100–150 mg indomethacin (an NSAID) or placebo to mild or moderately impaired Alzheimer's disease patients. These authors report that, based on a battery of cognitive tests, the indomethacin treatment appeared to protect those patients receiving indomethacin from the degree of cognitive decline exhibited by patients receiving placebo. If anything, this article, or any that have followed this article, suggests that the administration of indomethacin reduces the onset of dementia in Alzheimer's patients. Never has it been disclosed or suggested that the administration of indomethacin prevents the overproduction of APP.

Astrocytes upregulate expression of glial fibrillary acidic protein (GFAP) as they transform from a resting state into process-bearing reactive astrocytes during aging and in brain injury. Eddleston and Mucke, *Neurosci.,* 54, 15 (1993). GFAP levels are elevated in brain tissue and cerebrospinal fluid in AD [Wallin et al., *Dementia,* 7, 267 (1996)], suggesting that reactive astrocytes may contribute to the neuropathology. Furthermore, persistent and rapid elevations in APP immunoreactivity have been observed in GFAP-positive astrocytes following brain injury. Siman et al., *J.Neurosci.,* 3, 275 (1989); Banati and Kreutzberg, *J. Cereb. Blood Flow Metab.,* 12, 257 (1995). In the AD brain, the loss of synapses is associated with an increase in the number of GFAP-positive astrocytes [Brun et al., *Neurodegeneration,* 4, 171 (1995)], and increases in KPI-containing APP mRNA in the frontal cortex have also been attributed to the astrocytic response during neuronal damage [Golde et al., *Neuron,* 4, 253 (1990)]. It seems that the loss of synapses and neurons in AD might initiate a pathological cascade that includes APP synthesis by reactive astrocytes.

Cytosolic phospholipase $A_2$, which releases arachidonic acid from cellular phospholipids, is elevated in AD brain and after transient global ischemia. Stephenson et al., *Neurobiol. Disease,* 3, 51 (1996); Clemens et al., *Stroke,* 27, 527 (1996). The cyclooxygenation of arachidonic acid produces prostaglandins which, in turn, regulate neurotransmission, immune and inflammatory responses by activating receptors coupled to cAMP formation. Goetzl et al., *FASEB J.,* 9, 1051 (1995). We have discovered that cAMP elevations caused by activation of neurotransmitter receptors increased APP mRNA and holoprotein production in astrocytes. Lee et al., *PNAS USA,* 94, 5422 (1997). As discussed herein, it is now shown that activation of prostaglandin $E_2$ (PG $E_2$) receptors coupled to increased cAMP formation also stimulates the synthesis of APP mRNA and holoprotein. This effect appears to be mediated by cAMP-dependent protein kinases, and can be inhibited by various substances, including immunosuppressants and ion-channel modulators. Portions of this work have been presented as an abstract. Lee et al., *J.Neurochem.* (supp), 69, S103B (1997).

In U.S. Pat. No. 5,385,915, Buxbaum et al. describe methods and compositions for affecting APP processing by the administration of agents that regulate protein phosphorylation, namely agents that regulate kinases or phosphatases. The modulation of APP processing leads, in turn, to the regulation of the production of $\beta/A_4$ peptide, a peptide that accumulates in amyloidogenic plaques. See, e.g., col.6, lines 8–10. Hence, Buxbaum et al. teach that one's objective should focus on the search for agents that alter the metabolism of APP. They make no mention, teaching, or suggestion that the step preceding the processing of APP, that is, the expression, production, or formation of APP, itself, can be at all affected by select groups of substances. Indeed, as Buxbaum et al. state (at col. 21, lines 7–9), "the effects observed are attributable to changes in APP metabolism rather than APP transcription" (emphasis added). Consistent with this notion, the claims of Buxbaum et al. are drawn to a method of regulating phosphorylation of proteins that control the processing of APP.

Similarly, in U.S. Pat. No. 5,242,932, Gandy et al. disclose and claim a method of modulating or affecting the intracellular trafficking and processing of APP in the mammalian cell.

For additional background information on the processing of APP, release of APP derivatives, or the processing, degradation and secretion of $\beta/A_4$ APP, the interested reader is referred to the following publications: Nitsch, R. M. et al. *Science* (1992) 258:304; Lee, R. K. K. et al. *Proc. Nat'l. Acad. Sci. USA (*1995) 92:8083; Caporaso, G. L. et al. *Proc. Nat'l. Acad. Sci. USA* (1992) 89:3055; Caporaso, G. L. et al. *Proc. Nat'l. Acad. Sci. USA* (1992) 89:2252; and Buxbaum, J. D. et al. *Proc. Nat'l. Acad. Sci. USA* (1992) 89:10075.

Accordingly, it is an object of the present invention to provide methods and compositions that modulate or regulate the production or formation of APP in patients, including the expression of APP gene products and the transcription or translation of the APP gene in brain cells. For example, the production of APP by mammalian cells, in particular, by cells in the brain, can be increased or reduced.

In attaining this objective, it is also an objective of the invention to inhibit excessive amyloid formation, prevent neurite dystrophy and alleviate pathological symptoms, such as neurodegeneration or cognitive deficits that may arise from the negative effects of inappropriately expressed, produced, or formed amounts of APP.

Furthermore, the present invention seeks to provide compositions and methods that alleviate the detrimental effects of inappropriate APP production arising from overstimulation of receptors, particularly those coupled to cAMP formation.

It is also an object of the invention to provide relief from the debilitating effects of injury or trauma to the brain, as well as neurological diseases and neurodegenerative disorders, such as Alzheimer's, Parkinson's, or Lou Gehrig's Disease (amyotrophic lateral sclerosis), multiple sclerosis and the like, which may have their roots in the formation or presence of amyloid plaques.

3. SUMMARY OF THE INVENTION

It has now been discovered that prolonged activation of receptors that are coupled to increased cAMP formation in cortical astrocytes upregulates both APP mRNA levels and APP holoprotein bearing the KPI insert. It has further been discovered that such overproduction, which is shown can result from the body's response to brain injury or trauma, can be inhibited by certain substances, including agents that inhibit an inflammatory response and immune system suppressants.

In particular, it has been discovered that the immune or inflammatory response of astrocytes to brain injury accelerates the formation of amyloid plaques. It has also been shown that cAMP signaling regulates the astrocytic response to neuronal injury, while also stimulating transcriptional activation of the APP gene. Further, it is shown that prostaglandins, which are coupled to cAMP, also stimulate APP overexpression.

What is more, it has been shown that certain substances, including immune system suppressants (agents that inhibit an inflammatory response, and the like) inhibit this abnormal increase in APP synthesis (mRNA and cell-associated protein), which is caused by elevations in cAMP levels. Thus, these substances can be used to prevent APP overexpression in brain cells.

It has further been discovered that ion-gated channels can regulate APP overexpression. This is based on the observations, discussed herein, that the activation of nicotinic receptors in cultured astrocytes increases cellular levels of APP, as well as the observation that ion-channel modulators, such as calcium channel blockers and calcium/calmodulin kinase inhibitors, partially inhibit the stimulatory effect of prostaglandins on APP synthesis.

The present invention also contemplates and provides an assay for identifying or screening potential drugs that can inhibit the excessive or inappropriate production of amyloidogenic or neurotoxic APP fragments. For example, such an assay may utilize a tissue or cell culture comprising brain cells, as described herein.

The invention also contemplates a method by which the overexpression of APP is deliberately effected, followed by the promotion or stimulation of APP metabolism to provide soluble APP (APPs). The former step can be attained by, for example, cAMP signaling, while the latter process can be accomplished, for example, by the activation of protein kinase C (PKC) or of neurotransmitter agonists (e.g., via m1, m3, serotoninergic, or metabotropic glutamate receptors) which increase phophotidylinositol (PI) hydrolysis. Consequently, increased amounts of APPs are secreted into the medium, and the formation of amyloidogenic Aβ peptides is disrupted. It is believed that secreted APPs have neurotrophic and neuroprotective functions. Secreted APPs have been shown to promote neurite outgrowth and maintain synapse. It is believed further that increased APPs secretion promotes synaptic transmission and neuronal regeneration (e.g., via neurite or axonal outgrowth). The net result is the conversion of an amyloidogenic event (i.e., APP overexpression and Aβ formation) into a neurotrophic event (i.e., APPs secretion).

These and other objects of the invention will be evident to those of ordinary skill from a consideration of the discussions and descriptions provided in this specification, including the detailed description of the preferred embodiments.

4. BRIEF DESCRIPTION OF THE DRAWINGS

5. DETAILED DESCRIPTION OF THE PREFERRED EMBODIMENTS

Cultures of cortical astrocytes can be obtained from postnatal rats. See, e.g., K. D. McCarthy and J. de Vellis, *J. Cell Biol.* 85, 890 (1980).

The inventors have shown that the activation of adrenergic receptors present in the cortical astrocytes by 50 $\mu$M norepinephrine (NE) for a period of about 24 h increases the amount of cell-associated APP holoprotein by ~1.7-fold relative to amounts in untreated cells (See, FIG. 1, A), as measured using Western blots. The stimulatory effect of NE on total APP protein is inhibited by the β-adrenergic antagonist propranolol (50 $\mu$M) which, on its own, has no significant effect on basal APP protein levels.

Figure 1A:
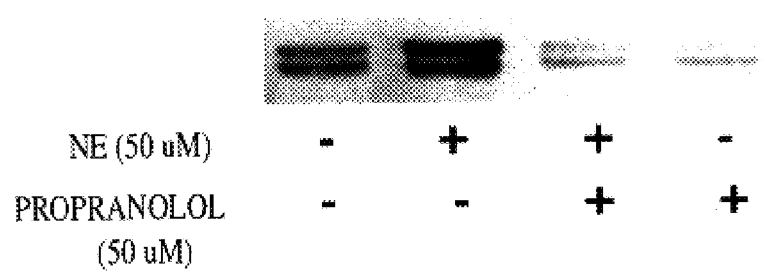
FIG. 1A illustrates the effects of norepinephrine (NE) and propranolol on the expression of cell-associated APP (APP holoprotein)
Figure 1B:
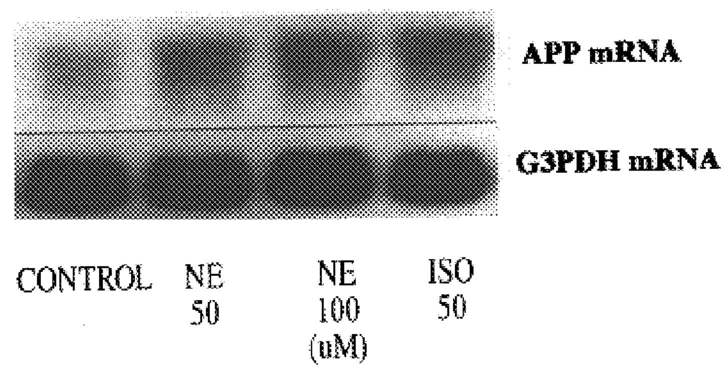
FIGS. 1B and 1C show that norepinephrine or the β-adrenergic agonist isoproterenol stimulates APP mRNA production, and that these stimulatory effects are abolished by the antagonist propranolol.
Figure 1C:
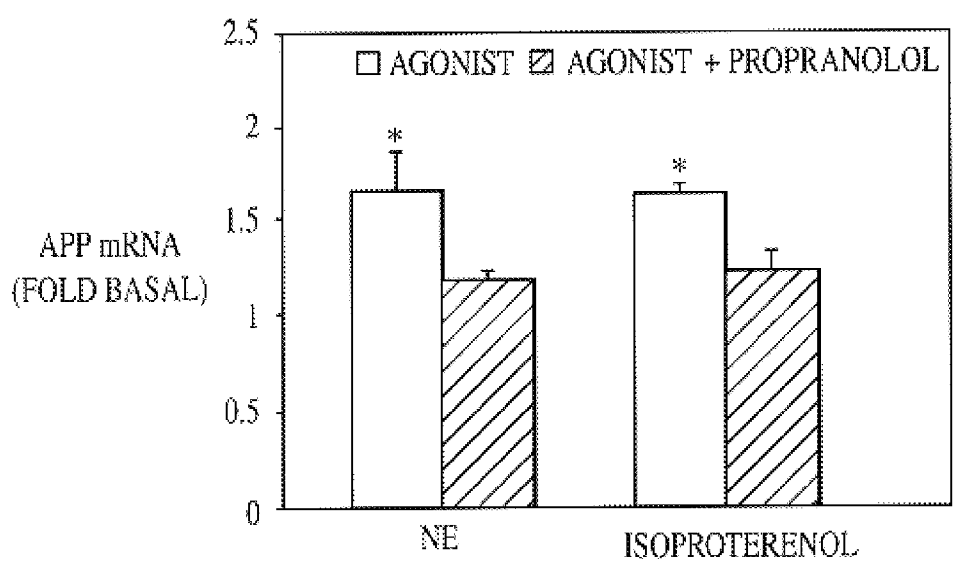

On Northern blots, APP mRNA levels are about 1.7-fold and about 1.6-fold higher after 24 h treatment with NE (50 or 100 $\mu$M) or the β-adrenergic agonist isoproterenol (50 $\mu$M), respectively, than those in untreated cells (FIG. 1, B); these increases are also abolished by 50 $\mu$M propranolol (FIG. 1, C). However, astrocytic levels of APP mRNA or of holoprotein do not increase linearly with increasing NE concentrations (50–400 $\mu$M). NE can stimulate cAMP formation and PI hydrolysis by activating β- or $\alpha_2$-adrenergic receptors, respectively. Propranolol (50 $\mu$M) inhibits the NE-induced (50 $\mu$M) increase in cAMP formation but not the increase in PI hydrolysis (FIG. 2), suggesting that activation of β-adrenergic receptors stimulates APP gene expression in cultured cortical astrocytes by enhancing cAMP synthesis.

Increases in β-adrenergic receptor density in the hippocampus and cortex of AD brain have been attributed by others to the proliferation of astrocytes. See, N. Kalaria et al., *J. Neurochem.* 53, 1772 (1989). Aberrant activation of these receptors, perhaps by circulating NE in AD or through a damaged blood-brain barrier, may cause abnormal cAMP signaling and, thus, APP overexpression in astrocytes.

In various cell lines, exposure to phorbol ester or to interleukin-1 can increase APP mRNA production by activating PKC and the AP-1 binding site on the APP promoter. See, D. Goldgaber et al., *Proc. Natl. Acad. Sci. U.S.A.,* 86, 7606 (1989).

Figure 3A:
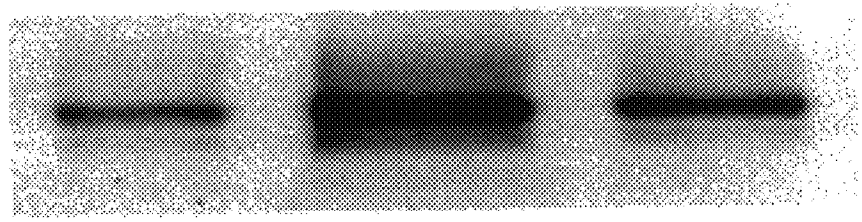
FIGS. 3A and 3B illustrate the effects of PMA and dexnorfenfluramine (DNF) on cell-associated APP and APPs secretion.
Figure 3B:
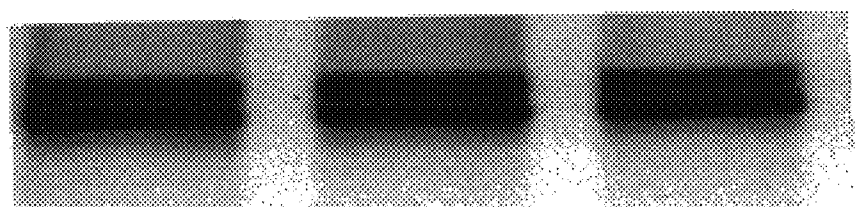

Since NE also increased PI hydrolysis, the second messengers diacylglycerol and inositol trisphosphate generated by PI hydrolysis could also have promoted APP expression in cortical astrocytes by activating PKC. However, direct activation of PKC by phorbol 12-myristate 13-acetate (5 $\mu$M) or activation of serotoninergic receptors by dexnorfenfluramine (100 EM), which also stimulates PI hydrolysis by ~2.6-fold relative to untreated astrocytes ($p<0.05$), does not increase APP mRNA or holoprotein levels but does increase APPs secretion by ~3.0- and ~2.2-fold, respectively, to that of untreated cells (FIG. 3). These results indicate that activation of PKC or of receptors coupled to PI hydrolysis does not stimulate APP synthesis in astrocytes but does promote APP metabolism.

To confirm that increased APP synthesis is mediated by elevations in cAMP levels caused by β-adrenergic receptor stimulation, the inventors have exposed astrocytes to the membrane-permeant 8-Bromo-cAMP (8Br-cAMP) or to the adenylate cyclase activator forskolin. The levels of APP holoprotein in astrocytes increases linearly with increasing concentrations of 8Br-cAMP or forskolin after 24. h treatment (FIG. 4) as revealed by the use of known monoclonal antibodies (mAb22C11) or antiserum (R37) directed against the N- or C-terminus of APP, respectively. The inventors have also shown from the use of the known antiserum R98, which recognizes an epitope of the KPI domain, that KPI-containing APP isoforms in cortical astrocytes are also increased by treatments that elevate cAMP levels.

Figure 5A:
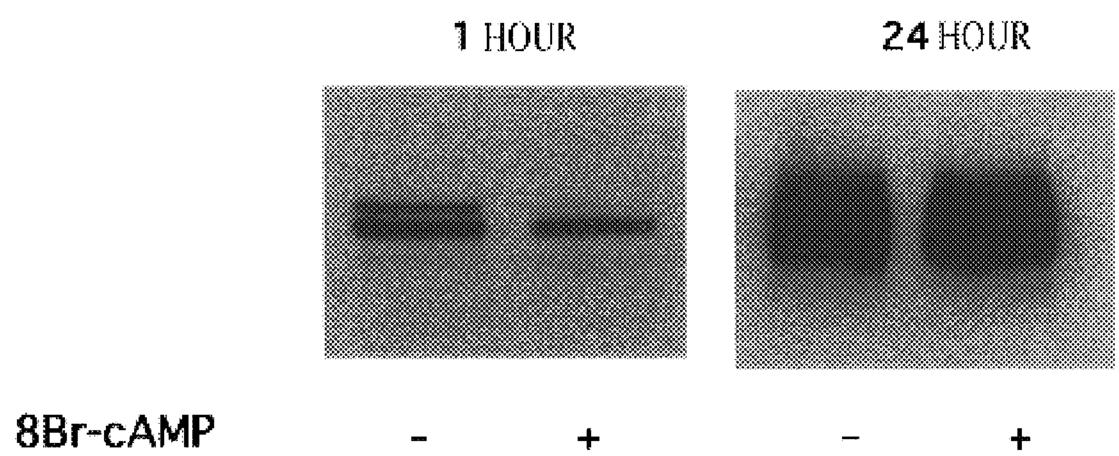
FIGS. 5A and 5B illustrate the effects of 8Br-cAMP on APPs secretion from cultured astrocytes.
Figure 5B:
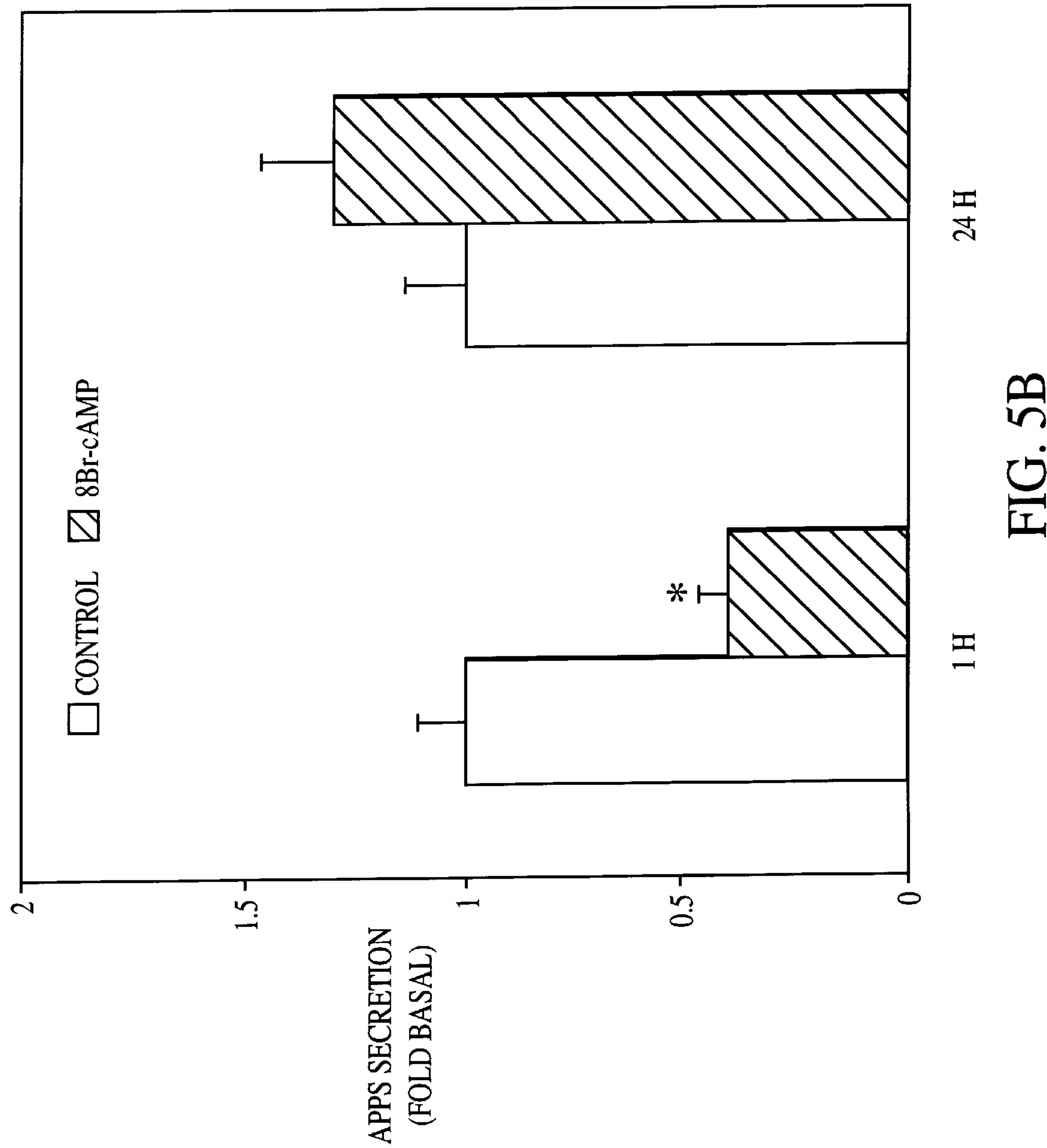
Figure 6:
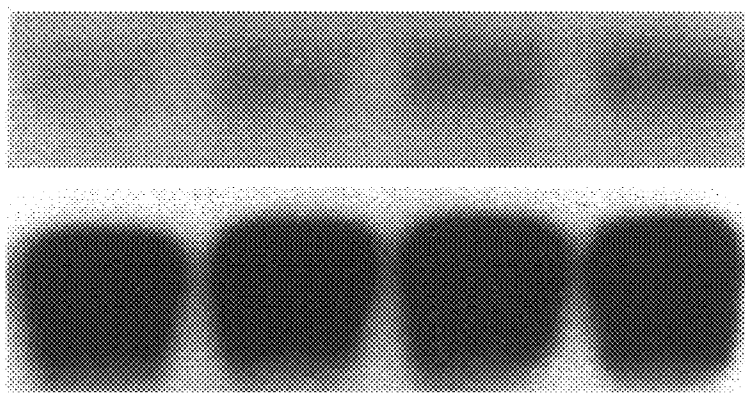
FIG. 6 illustrates the effect of 8Br-cAMP on APP mRNA.

APPs levels in astrocytes that are treated with or without 8Br-cAMP (250 $\mu$M) for 24 h do not differ significantly ($p>0.05$), suggesting that decreases in APP metabolism do not account for the increase in astrocytic APP protein that is observed with 8Br-cAMP treatment FIGS. 5A and 5B. Northern blot analyses show that treatment with 250 $\mu$M 8Br-cAMP for 24 h increases astrocytic APP mRNA levels to ~1.8-fold those of untreated cells (FIG. 6). This result indicates that prolonged (~24 h) cAMP signaling in cultured astrocytes can stimulate APP synthesis by transcriptional activation. Although exposure to 50 or 100 $\mu$M 8Br-cAMP occasionally increases APP mRNA, these effects are not consistent. No significant changes in APP mRNA levels are detected after 6 h or 12 h treatment with 8Br-cAMP (250 $\mu$M). The inventors have also observed that the APP transcript in astrocytes treated with or without 8Br-cAMP has a slower mobility than that observed in neurons. Hence, the APP mRNA that is upregulated by 8Br-cAMP treatment may contain the KPI motif.

Figure 7:
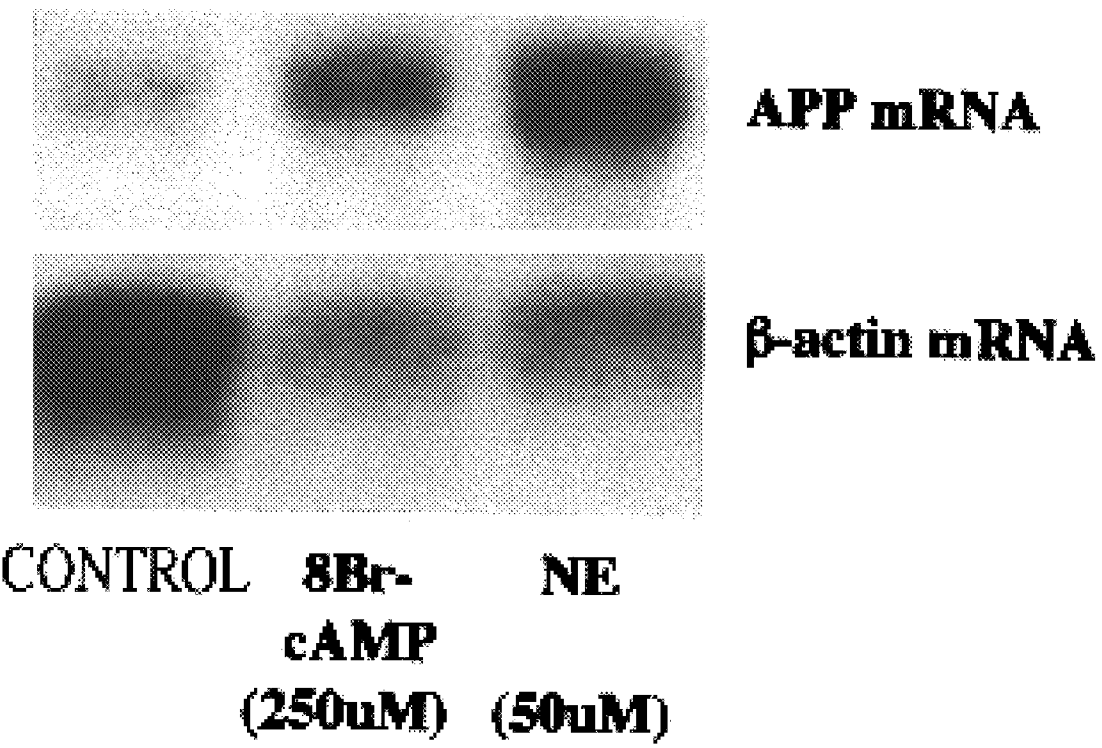
FIG. 7 illustrates the effects of 8Br-cAMP or NE on actin and APP mRNA.
Figure 8:
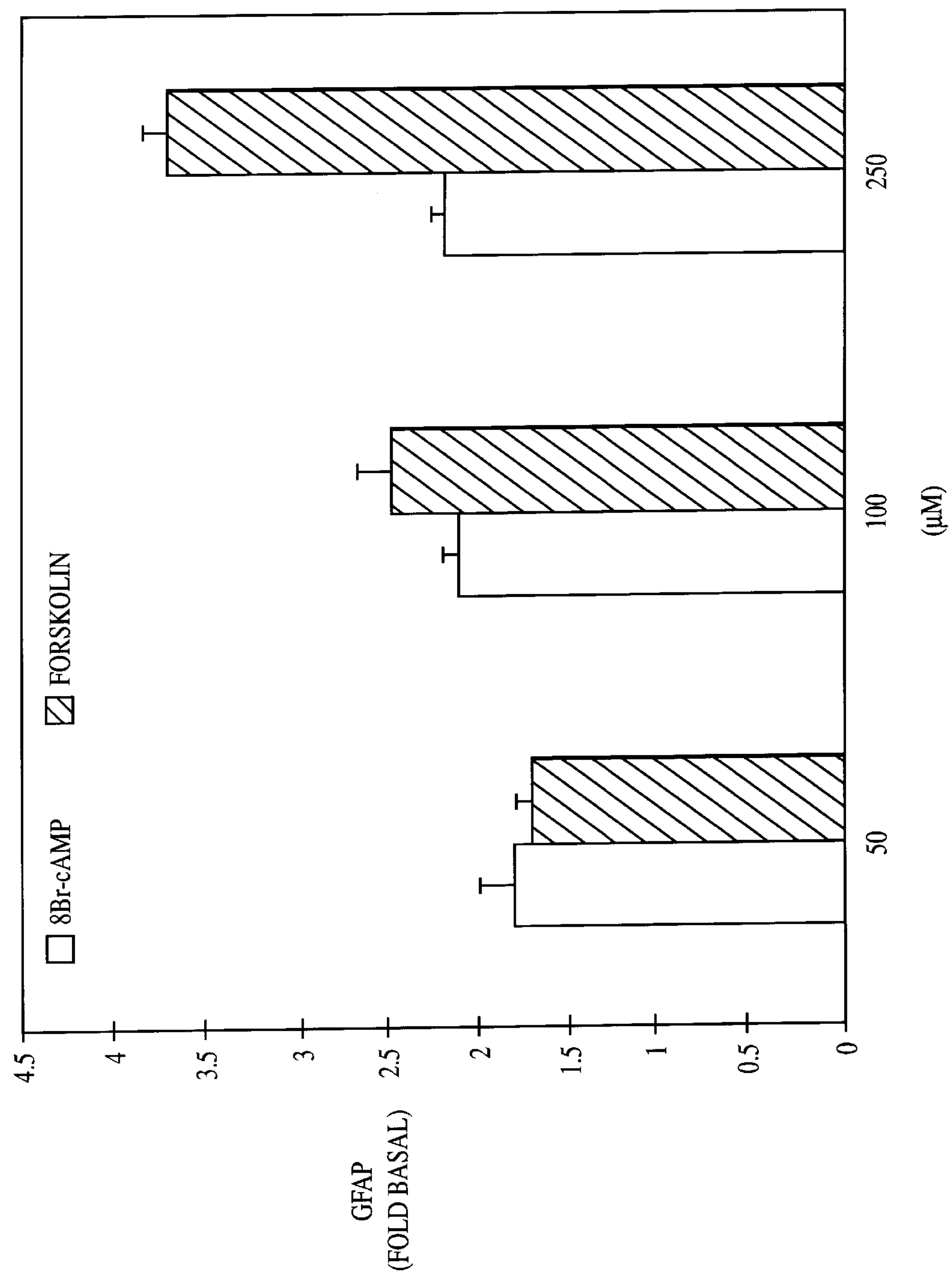
FIG. 8 illustrates the effects of forskolin or 8Br-cAMP on GFAP expression in cultured astrocytes.

The increases in APP mRNA that is caused by 8Br-cAMP (250 $\mu$M) or NE (50 $\mu$M) are associated with decreases in levels of mRNA for β-actin (FIG. 7). The downregulation of cytoskeletal stress fibres, such as actin, may be related to the morphological differentiation of astrocytes from flat, polygonal cells to process-bearing, stellate cells. Moreover, GFAP expression in cultured astrocytes is also increased by elevations in cAMP levels (FIG. 4; FIG. 8). These morphological and biochemical changes that are induced by 8Br-cAMP in cultured astrocytes resemble the gliotic response of astrocytes in vivo. These findings thus suggest that the increased APP immunoreactivity in astrocytes after neuronal injury results from increased APP gene expression rather than from the internalization of exogenous APP that are released from dying cells. It is noted that Gegelashvili et al. reported that treatment with dibutyryl cAMP in serum-containing medium increased APP mRNA in rat glioma cells but not in cortical astrocytes. See, G. Gegelashvili, E. Bock, A. Schousboe, D. Linnemann. *Mol. Brain. Res.* 37, 151 (1996). Apparently, the stimulatory effect of cAMP on APP synthesis in cortical astrocytes of the present invention is related to the use of serum-deprived cells.

Figure 9A:
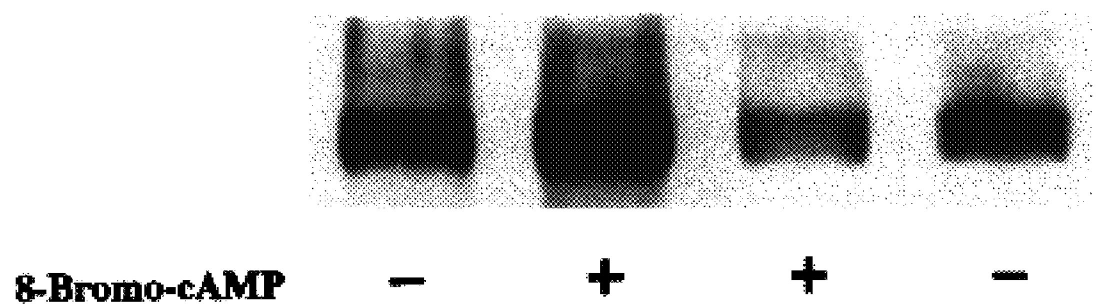
FIGS. 9A, 9B and 9C illustrate the effect of cyclosporin A on APPs secretion and cell-associated APP, in the absence or presence of 8Br-cAMP.
Figure 9B:
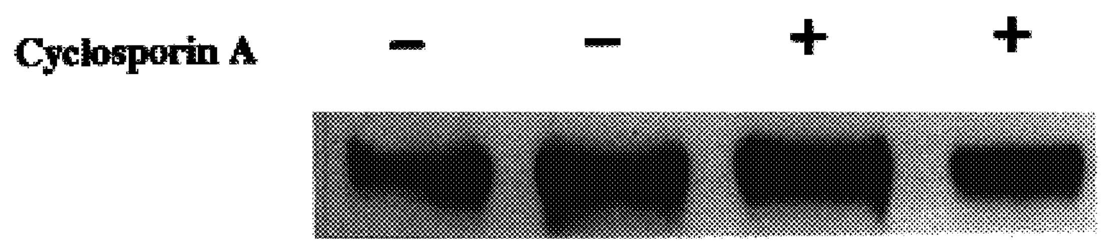
Figure 9C:
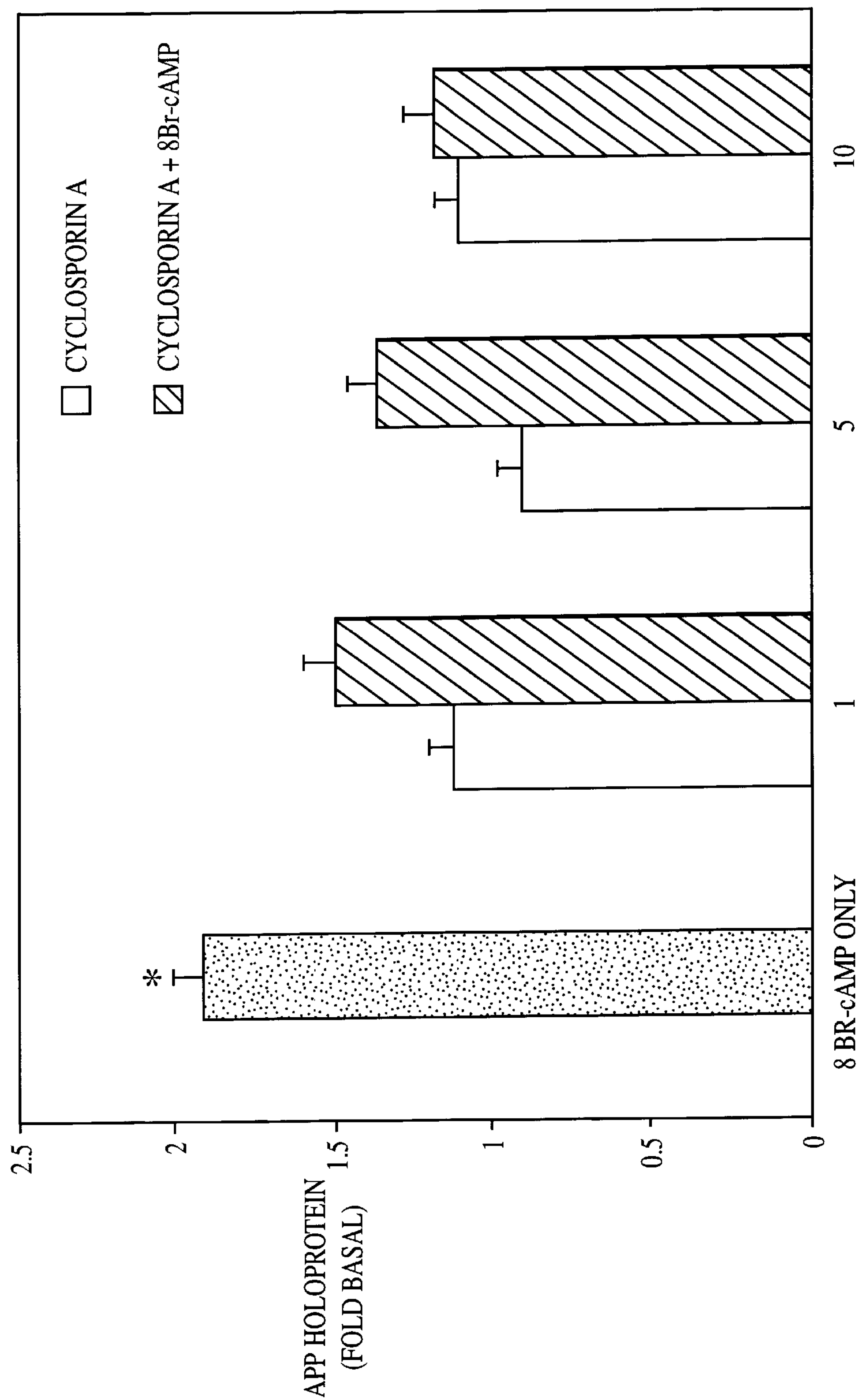

Induction of gene transcription by cAMP can be inhibited by the immunosuppressant cyclosporin A. In cortical astrocytes, cyclosporin A (1, 5, or 10 $\mu$M) inhibits the increase in APP mRNA and APP holoprotein which is caused by 24 h exposure to 8Br-cAMP (250 $\mu$M). The inhibitory effects of 1, 5, or 10 $\mu$M cyclosporin A do not differ significantly (FIG. 9). Basal APP holoprotein levels, APPs secretion and GFAP expression also are unaffected by these concentrations of cyclosporin A ($p>0.05$). Hence, immunosuppressants such as cyclosporin A exhibit a potential usefulness for preventing aberrant APP expression in AD.

The results reported herein further show that activation of PG $E_2$ receptors coupled to cAMP formation stimulates APP gene expression in cultured cortical astrocytes. Increases in APP mRNA and holoprotein were detected with 1, 10 or 100 $\mu$M PG $E_2$ treatment of astrocytes for 24 h. Shorter duration treatment (6 or 12 h) with 10 $\mu$M PG $E_2$ did not reliably increase APP synthesis (unpublished data). Because about 95% of the cells in our cultures express proteins specific for astrocytes but not for neurons or microglia [Lee and Wurtman, *J.Neurochem.,* 68, 1830 (1997)], we suggest the increased APP mRNA and holoprotein observed after PG $E_2$ treatments originates from astrocytes. Since APP overexpression causes symptoms of AD [Cordell, *Annu.Rev.Pharmacol.Toxicol.,* 34, 69 (1994); Yoshikawa et al., *Nature,* 359, 64 (1992); Hsiao et al., *Neuron,* 15, 1203 (1995)], it seems that increased APP synthesis in astrocytes stimulated by PG $E_2$ may accelerate neuropathology, and the formation of amyloidogenic and neurotoxic peptides.

Alternative splicing of the APP gene yields several APP isoforms of vary sizes. Kang et al., *Nature,* 325, 733 (1987); Oltersdorf et al., *Nature,* 341, 144 (1989); van Nostrand et al., *Nature,* 341, 546 (1989). APP695 which lacks the KPI-motif is the major isoforms found in the brain. Astrocytes and microglia, both of which express APP751/770 isoforms containing the KPI domain, express only low levels of APP mRNA and protein in the resting state but upregulate KPI-containing APP isoforms following brain injury or neurodegeneration. Siman et al., *J.Neurosci.,* 3, 275 (1989); Sola et al., *Mol. Brain Res.,* 17, 41 (1993); Banati et al., *J.Cereb.Blood Flow Metab.,* 12, 257 (1995). Our labelled APP cDNA probe did not distinguish between the various kinds of APP transcripts on Northern blots. However, Western blot analyses using antiserum R98 [Kametani et al., *Biochem. Biomed. Res. Comm.,* 191, 392 (1993)] revealed increases in KPI-containing APP isoforms following PG $E_2$ treatments. Increases in cellular APP holoprotein were also detected by antisera R37 directed at the C-terminus of APP, indicating that the KPI-containing APP increased by astrocytes are full-length holoproteins harboring intact and potentially amyloidogenic Aβ peptides. Since mAb22C11 recognizes the N-termini of both APP and APP-like proteins [Weidemann et al., *Cell,* 57, 115 (1989); Slunt et al., *J.Biol.Chem.,* 269, 2637 (1994)], it is possible that PG $E_2$ treatment may also stimulate transcriptional regulation of other members of the APP gene family.

APP synthesis in astrocytes is probably mediated by the increases in cAMP production stimulated by PG $E_2$ treatment. Concentration-dependent elevations in cAMP were observed after treatment with 1, 10 or 100 μM PG $E_2$ but not with 0.1 μM PG $E_2$. Similarly, 1, 10 or 100 but not 0.1 μM PG $E_2$ stimulated increases in APP mRNA and holoprotein. Furthermore, the stimulatory effect of PG $E_2$ on APP synthesis was also mimicked by membrane-permeant 8Br-cAMP (250 μM) or by activating adenylate cyclase with forskolin (10, 50 or 100 μM). Elevations in cAMP activate cAMP-dependent protein kinase (PKA) which, in turn, phosphorylates proteins involved in regulating gene expression. In our study, activation of PKA by Sp-cAMP triethylamine in the absence of PG $E_2$ was sufficient to stimulate increases in astrocytic APP holoprotein. Furthermore, inhibition of protein kinase A by H-89 dihydrochloride blocked the stimulatory effect of PG $E_2$ on APP mRNA production. These data provide strong support for PKA in mediating the stimulatory effect of cAMP on APP synthesis.

The APP promoter contains several sequences for regulatory elements that are responsive to cAMP signalling. Salbaum et al., *EMBO J.,* 7, 2807 (1988). PKA can phosphorylate cAMP response element binding protein (CREB) to stimulate gene expression. While there is no canonical sequence for CREB (TGACGTCA) within the 3.7-kb region upstream of the APP transcription start site [Salbaum et al., ibid], a consensus sequence for CREB (TGACCTCA) could be responsible for initiating APP synthesis in astrocytes. Elevations in cAMP may also induce c-fos and c-jun expression to activate APP synthesis through AP-1 recognition sites. However, APP synthesis in NG108-15 and HepG2 cells stimulated by dibutyryl cAMP appears not to depend on the presence of AP-1 or AP-2 sites. Bourbonniere et al., *J.Neurochem.,* 68, 909 (1997); Shekarabi et al., *J.Neurochem.,* 68, 970 (1997). Nevertheless, at least two other cAMP-responsive regions have been identified within the APP promoter of NG-108 cells [Bourbonniére et al., ibid]. It is not known if these cis-acting regulators are functional for regulating cAMP responsiveness in astrocytes, or if the induction of APP synthesis is mediated by trans-acting elements acting through the expression of other cAMP-responsive genes.

The immunosuppressants cyclosporin A and FK-506 are inhibitors of calcineurin and can suppress gene activation stimulated by cAMP. Schwaninger et al., *J.Biol.Chem.,* 270, 8860 (1995). We previously found that cyclosporin A inhibited APP synthesis in astrocytes treated with 8-Bromo-cAMP but we did not determine if cyclosporin A would inhibit APP synthesis stimulated by first messengers. Lee et al., *PNAS USA,* 94, 5422 (1997). We now show that cyclosporin A or FK-506 completely abolished APP overexpression stimulated by PG $E_2$ or by forskolin. Both cyclosporin A and FK-506 bind to intracellular immunophilin receptors that are not known to directly affect cAMP production. Clardy, *PNAS USA,* 92, 56 (1995). As expected, neither cyclosporin A nor FK-506 had any effect on basal cAMP levels in cultured astrocytes, and neither drug inhibited the increase in cAMP caused by PG $E_2$. Hence, the inhibitory effect of cyclosporin A or FK-506 appears to lie downstream of cAMP production and possibly by interfering directly with gene transcription. Although cyclosporin A and FK-506 are potent immunosuppressive drugs generally used to prevent rejection of organ transplants and autoimmune diseases, our data suggest that both these immunosuppressants may be useful for preventing aberrant APP overexpression.

AD is not usually considered to be an inflammatory or immune disease. However, increased lipid peroxidation and formation of prostaglandins have been reported in AD. Iwamoto et al., *J.Neurol.,* 236, 80 (1989); Subbarao et al., *J.Neurochem.,* 55, 342 (1990). In addition, all major components of the classical complement pathway appear to be associated with AD lesions, suggesting that neuronal damage or amyloid deposits may trigger inflammatory or immune processes and accelerate neuropathology. McGeer and McGeer, *Brain Res.Rev.,* 21, 195 (1995). Epidemiological data provide strong circumstantial evidence that anti-inflammatory therapies such as the use of non-steroidal anti-inflammatory drugs or dapsone may be effective in slowing the progression of neuropathology in AD. McGeer and McGeer, ibid. The results presented herein suggest that anti-inflammatory agents such as indomethacin or inhibitors of prostaglandin G/H synthase (cyclooxygenase) which prevent the synthesis of prostaglandins from arachidonic acid can prevent the production of amyloid and neurotoxic APP fragments associated with APP overexpression in astrocytes.

Treatment with PG $E_2$ induced process formation and also increased the levels of GFAP in our cultured astrocytes. Both these effects are probably mediated by elevations in cAMP caused by PG $E_2$. The disruption of cytoskeletal fibers associated with morphological transformation into GFAP-positive and process-bearing cells was associated with decreased levels of β-actin mRNA [Lee et al., *PNAS USA,* 94, 5422 (1997)], suggesting that these cultured astrocytes resemble reactive astrocytes. Rapid and persistent increases in APP immunoreactivity in GFAP-positive reactive astrocytes have been observed after brain lesions or ischemia. Siman et al., *J.Neurosci.,* 3, 275 (1989); Banati et al., (1996). Although the phagocytic activity of astrocytes or microglia can increase APP immunoreactivity [Paresce et al., *Neuron,* 17, 553 (1996)], our study suggests that GFAP-positive astrocytes can actively upregulate APP synthesis following brain injury.

The loss of synapses has been suggested to be an early event in the pathology of AD, and appears to be related to the extent of reactive astrogliosis. Brun et al., *Neurodegeneration,* 4, 171, (1995); Heionen et al., *Neuroscience,* 64, 375 (1995). The invasion and proliferation of reactive astrocytes within these regions of degeneration may explain the increased levels of GFAP in the brain tissue and cerebrospinal fluid of AD. Wallin et al., (1995). Indeed, the upregulation of β-adrenergic receptors in the frontal cortex and hippocampus of AD brains has been attributed to the proliferation of astrocytes associated with neurodegeneration. Kalaria et al., *J.Neurochem.,* 53, 1772 (1989). Circulating levels of norepinephrine after brain injury appear to cause reactive astrogliosis and cell proliferation. Hodges-Savola et al., *Glia,* 17, 52 (1996). We suggested that the aberrant activation of β-adrenergic receptors coupled to cAMP signalling by norepinephrine might also stimulate APP overexpression in astrocytes. Lee et al., (1997). These studies, together with our present finding that activation of PG $E_2$ receptors can stimulate APP synthesis, underscore the contribution of receptor activation in the overproduction of APP.

APP overexpression in cultured astrocytes treated with PG $E_2$ was associated with the secretion of APP holoprotein. Although secreted APP is usually truncated at the C-terminus, antisera C8 which is directed at the C-terminus of APP [Selkoe et al., *PNAS USA,* 85, 7341 (1988)] detected increased amounts of APP holoprotein (~130 kD) in the media of astrocytes treated with PG $E_2$ for 24 h. The present findings are consistent with the observation that Chinese hamster ovary cells transfected with full-length APP751 cDNA also secrete soluble APP holoprotein. Eftimiopoulos et al., (1996). APP holoprotein can be detected in the cerebrospinal fluid of humans, and can be actively released from secretory vescicles in response to receptor stimulation or neuronal depolarization. It is not known if secreted APP holoprotein is reinternalized for subsequent processing, or if it can be metabolized in the extracellular space.

The increase in KPI-containing mRNAs in the frontal cortex of AD patients that are not usually expressed in the brains [Golde et al., *Neuron,* 4, 253 (1990); Tanaka et al., *Biochem.Biophys.Res.Comun.,* 165, 1406 (1989)], suggest that APP isoforms with and without KPI domains have different functions in the nervous system. The KPI domain of APP is highly homologous to the Kunitz-type of serine protease inhibitors, and secreted APP isoforms containing the KPI domain has been identified as protease nexin II. Oltersdorf et al., *Nature,* 341, 144 (1989); van Nostrand et al., *Nature,* 341, 546 (1989). Protease inhibitors expressed by reactive astrocytes can also form protease-protease inhibitor complexes to induce the synthesis of cytokines, acute phase protein and the migration of neurotrophils which can further promote brain injury and inflammation. Eddleston and Mucke, *Neurosci.,* 54, 15 (1993). Although APP overexpression can cause neurological disorders [Yoshikawa et al., *Nature,* 359, 64 (1992); Cordell, *Annu. Rev. Pharmacol. Toxicol.,* 34, 69 (1994); Hsiao, *Neuron,* 15, 1203, (1995)], secreted and cell-associated APP may have mitogenic, neuroprotective or neurotrophic properties. Saitoh et al., *Cell,* 58, 615 (1989); Schubert et al., *Neuron,* 3, 689 (1989); Mattson et al., *Trends Neurosci.,* 16, 409 (1993). In particular, the finding that APP751 promotes neurite formation and tau expression in primary neuronal cultures [Qiu et al., *J.Neurosci.,* 2157 (1995); Lee et al., *PNAS USA,* 92, 8083 (1995)] suggests that overexpression of astrocytic APP may have effects on neuronal growth and survival in the brain. Whether such neurotrophic activities can contribute to brain regeneration or to aberrant neurite outgrowth remains to be determined.

Our findings show that PG $E_2$ can stimulate GFAP expression, APP synthesis and the release of amyloidogenic APP holoprotein from cultured astrocytes. APP overexpression in DS and in transgenic mice is associated with the pathologic symptoms of AD. To the extent that astrocytes proliferate and upregulate APP synthesis during aging and neuronal injury, non-neuronal cells may contribute to the neuronal dysfunction and the pathology of AD. Therefore, it seems that inhibition of prostaglandin synthesis by anti-inflammatory agents or by inhibitors of phospholipase $A_2$ ($PLA_2$) may prevent APP overexpression and its associated pathologies. In particular, we suggest that immunosuppressants such as cyclosporin A or FK-506 may be especially useful in preventing transcriptional activation of APP and, possibly, the progression of AD.

In summary, the present studies show that stimulation of adrenergic receptors coupled to cAMP formation in astrocytes increases the production of APP mRNA and APP holoprotein. It is suggested that the upregulation or aberrant activation of $\beta_2$-adrenergic receptors in brain regions that are vulnerable to damage can stimulate transcriptional activation of APP synthesis in astrocytes and, thereby, contribute to amyloid production. Because APP overexpression can cause neurodegeneration and cognitive dysfunction, the inventors have shown that such substances as propranolol or immunosuppressants, e.g., cyclosporin A, FK-506, ion channel modulators, e.g., EGTA, calcium/calmodulin kinase inhibitors, e.g., KN-95, and the like, are promising drug candidates for the treatment of AD.

5.1. Further Aspects of the Preferred Embodiments

Thus, the present invention is directed to a method of modulating the expression, production, or formation of amyloid precursor protein (APP) in a subject comprising administering to the subject an effective amount of cyclic adenosine monophosphate (cAMP), an analog of cAMP, a substance that is a ligand, an agonist, or an antagonist of a receptor that is coupled to the cellular levels of cAMP or to ion channels, a compound that regulates ion channels or the nuclear actions of cAMP, or a compound that regulates the activity of protein kinase A. In specific embodiments of the invention the analog of cAMP can comprise 8Br-cAMP, the ligand can comprise norepinephrine, the agonist can comprise isoproterenol, and the antagonist can comprise propranolol.

By "nuclear actions" is meant any activity of cAMP that is exerted in the nucleus of a eukaryotic cell that ultimately gives rise to changes in the expression, production, formation, metabolism, or amount of APP in a subject, including but not limited to the regulation of the promoter of the APP gene, the modulation of transcription factors that affect APP expression, or the stimulation of the activity of cAMP-dependent protein kinase.

Indeed, according to the methods of the present invention, a suitable antagonist can comprise a receptor antagonist of a neurotransmitter, a modulator of signal transduction, an immunosuppressant, an anti-inflammatory agent, or combinations thereof. In a preferred embodiment, the modulator selected can modulate the activity of protein kinase A but does not activate protein kinase C. Still in other embodiments the modulator selected does not activate phosphate activity. However, as discussed further below, in a multistep process having at least two or more steps, the expression, production, or formation of APP can be modulated in an initial or first step, followed by the modulation of kinase or phosphatase activity with the objective, for example, of processing or metabolizing overproduced APP into nonamyloidogenic or neurotrophic metabolic products.

In the inventive method the ligand, agonist, or antagonist of a receptor can be those substances that bind or exhibit an affinity for a receptor that can comprise a adrenergic, serotoninergic, dopaminergic, adenosine, vassopressin intestinal peptide, pituitary adenylate cyclase activating peptide (PACAP), prostaglandin $E_2$, histamine, muscarinic, nicotinic, opioid, GABA, or metabotropic glutamate receptor.

The following kinase stimulators are also suitable for use in the present invention, including staurosporine, auranofin, N-(6-aminohexyl)-1-naphthalen-sulfonamide hydrochloride, N-(4-aminobutyl)-2-naphthalenesulfonamide hydrochloride, N-(4-aminobutyl)-5-chloro-2-naphthalenesulfonamide hydrochloride, N-(6-aminohexyl)-5-chloro-1-naphthalenesulfonamide hydrochloride, 1-(5-isoquinolinesulfonyl)-2-methylpiperazine dihydrochloride, N-(2-(methylamino) ethyl)-3-isoquinolinesulfonamide dihydrochloride, N-(2-aminoethyl)-5-isoquinolinesulfonamide, N-(2-guanidinoethyl)-5-isoquinolinesulfonamide hydrochloride, sphingosine and tyrphostin.

Examples of additional substances, which have been found to decrease or inhibit the APP synthesis include, but are not limited to H8, H9, cyclosporin A, FK-506, Win55212, and propranolol. The inhibitory effects of the latter two compounds are most evident when the basal levels of APP synthesis have been upregulated. For the stimulation of protein kinase A (PKA), the preferred substance can comprise Sp-cAMPS triethylamine.

In practicing the disclosed method or using the disclosed compositions the synthesis of endogenous APP can be stimulated or, alternatively, suppressed. When APP is desirably overproduced, the overproduction can be effected a by increasing the levels of cellular cAMP. The increase in the levels of cellular cAMP can, in turn, be effected by exposing or administering to the subject effective amounts of exogenous cAMP. Preferably, the exposure or administration is performed for a continuous period. The continuous period may be any suitable or practical length of time but, preferably, at least about six hours, at least about twelve hours, at least about twenty-four hours or more.

An increase in the levels of cellular cAMP can also be effected by stimulating the synthesis of endogenous cAMP or by retarding the breakdown of cAMP. In a preferred embodiment of the invention, the synthesis of endogenous cAMP is stimulated by administering an effective amount of a prostaglandin, such as prostaglandin $E_2$, and the like. Other compounds that can be used to this end include forskolin and a nicotinic agonist, e.g., nicotine or a salt thereof, such as nicotinic ditartrate.

When it is desirable to effect a decrease of endogenous APP production, cellular levels of cAMP are caused to diminish. For example, the cellular levels of cAMP can be decreased by retarding the synthesis of endogenous cAMP or by stimulating the breakdown of cAMP. Substances, such as H8, H9, propranolol, or Win55212 can be administered to achieve this end. Also, ion-channel modulators, e.g., calcium channel blockers, including chelating agents such as EGTA, and calcium/calmodulin kinase inhibitors, such as KN93, can be employed.

In still another embodiment of the present invention, the production of APP is first enhanced, followed by the stimulation of APP processing or metabolism. The latter step can be accomplished by administering an effective amount of a substance that stimulates protein kinase C (PKC) activation, activation of phosphatases, or phosphatidyl inositol (PI) hydrolysis. The objective is the conversion of an amyloidogenic event (APP overexpression) to a neurotrophic event (the secretion of APPs or other nonamyloidogenic by-products). In particular, the stimulation of PKC, for example, can be achieved with the administration of effective amounts of phorbol ester or diacylglycerol.

The present invention also contemplates a method of modulating the production of amyloid precursor protein (APP) in a subject comprising regulating the expression of glial fibrillary acidic protein (GFAP) in the subject. Preferably, the production of APP is enhanced by stimulating the transcription or translation of GFAP mRNA. Conversely, the production of APP is diminished by inhibiting the transcription or translation of GFAP mRNA.

As in the methods described above, GFAP expression can be regulated by administering to the subject an effective amount of an anti-inflammatory agent, which are preferably selected from a corticosteroid, glucocorticoid, or an admixture comprising estrogen and estradiol.

An important aspect of the present invention concerns the treatment of a subject that has suffered an injury or trauma, especially to the head or brain, or of a subject that is, for some other or related reason, may be experiencing overstimulation of cAMP expression, production, formation (or, collectively, "synthesis").

It is particularly advantageous to treat the subject in need by administering an effective amount of an immune system suppressant, such as cyclosporin A or other similar suppressant.

It is noteworthy that the present invention is also directed to a method of determining the capacity of a drug to inhibit the expression, production, or formation of amyloid precursor protein (APP) in a cell comprising contacting a drug with a cell culture that has been exposed to cyclic adenosine monophosphate (cAMP), an analog of cAMP, a substance that is a ligand, an agonist, or an antagonist of a receptor that is coupled to the cellular levels of cAMP, a compound that regulates the nuclear actions of cAMP, or a compound that regulates the activity of protein kinase A. The level of mRNA or holoprotein produced from the cell culture in the presence of the drug is then compared with the level of mRNA or holoprotein produced from the cell culture in the absence of the drug. The cell can be any type of microbial, plant, or animal cell, so long as the cell has the capacity to express, produce, or otherwise form APP. The cell is preferably a eukaryotic cell. More preferably, the eukaryotic cell can further be a yeast cell, insect cell, invertebrate, vertebrate, or mammalian, including animal or human.

It should be apparent that the present invention is directed to a method of alleviating the negative effects of a neurological disorder or neurodegenerative disease stemming from the aberrant expression, production, or formation of amyloid precursor protein (APP) in a subject. In a particular embodiment, an effective amount of an antagonist of a β-adrenergic receptor, which is coupled to the cellular levels of cAMP, is administered to the subject suffering from the disorder or disease. As described herein, the antagonist may comprise a receptor antagonist of a neurotransmitter, a modulator of signal transduction, an immunosuppressant, an anti-inflammatory agent, or combinations thereof, preferably provided that the modulator does not activate protein kinase C.

It should also be apparent the present method of modulating amyloid precursor protein (APP) expression in a subject may also comprise administering to the subject an effective amount of a substance that regulates APP promoter activity, either by stimulating APP promoter activity or retarding it.

The inhibition of APP promoter activity can, in turn, regulate the expression of abnormal forms of tau. And, hence, the present invention also contemplates a method of regulating the expression of abnormal forms of tau in a subject comprising modulating amyloid precursor protein (APP) expression in the subject.

Moreover, compositions for modulating the expression, production, or formation of amyloid precursor protein (APP) in a subject are intended which comprise a carrier and cyclic adenosine monophosphate (cAMP), an analog of cAMP, a substance that is a ligand, an agonist, or an antagonist of a receptor coupled to the cellular levels of cAMP or to ion channels, a compound that regulates the nuclear actions of cAMP or ion channels, or a compound that regulates the activity of protein kinase A.

5.2. Compositions of the Present Invention

As should be apparent, the present invention also contemplates compositions comprising the active substances disclosed herein. Preferably, these compositions include pharmaceutical compositions comprising a therapeutically effective amount of one or more of the active compounds or substances along with a pharmaceutically acceptable carrier.

As used herein, the term "pharmaceutically acceptable" carrier means a non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations.

Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Examples of pharmaceutically acceptable antioxidants include, but are not limited to, water soluble antioxidants such as ascorbic acid, cysteine hydrochloride, sodium bisulfite, sodium metabisulfite, sodium sulfite, and the like; oil soluble antioxidants, such as ascorbyl palmitate, butylated hydroxyanisole (BHA), butylated hydroxytoluene (BHT), lecithin, propyl gallate, alohatocopherol and the like; and the metal chelating agents such as citric acid, ethylenediamine tetraacetic acid (EDTA), sorbitol, tartaric acid, phosphoric acid and the like.

By a "therapeutically effective amount" or simply "effective amount" of an active compound, such as an analog of cAMP, is meant a sufficient amount of the compound to treat or alleviate the negative effects of a neurological disorder or neurodegenerative disease stemming from the aberrant expression, production, or formation of amyloid precursor protein (APP) at a reasonable benefit/risk ratio applicable to any medical treatment. It will be understood, however, that the total daily usage of the active compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coinciding with the specific compound employed; and like factors well known in the medical arts.

The total daily dose of the active compounds of the present invention administered to a subject in single or in divided doses can be in amounts, for example, from 0.01 to 25 mg/kg body weight or more usually from 0.1 to 15 mg/kg body weight. Single dose compositions may contain such amounts or submultiples thereof to make up the daily dose. In general, treatment regimens according to the present invention comprise administration to a human or other mammal in need of such treatment from about 1 mg to about 1000 mg of the active substance(s) of this invention per day in multiple doses or in a single dose of from 1 mg, 5 mg, 10 mg, 100 mg, 500 mg or 1000 mg.

In certain situations, it may be important to maintain a fairly high dose of the active agent in the blood stream of the patient, particularly early in the treatment. Hence, at least initially, it may be important to keep the dose relatively high and/or at a substantially constant level for a given period of time, preferably, at least about six or more hours, more preferably, at least about twelve or more hours and, most preferably, at least about twenty-four or more hours.

The compounds of the present invention may be administered alone or in combination or in concurrent therapy with other agents which affect the central or peripheral nervous system, particularly selected areas of the brain.

Liquid dosage forms for oral administration may include pharmaceutically acceptable emulsions, microemulsions, solutions, suspensions, syrups and elixirs containing inert diluents commonly used in the art, such as water, isotonic solutions, or saline. Such compositions may also comprise adjuvants, such as wetting agents; emulsifying and suspending agents; sweetening, flavoring and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulation can be sterilized, for example, by filtration through a bacteria-retaining filter, or by incorporating sterilizing agents in the form of sterile solid compositions, which can be dissolved or dispersed in sterile water or other sterile injectable medium just prior to use.

In order to prolong the effect of a drug, it is often desirable to slow the absorption of a drug from subcutaneous or intramuscular injection. The most common way to accomplish this is to inject a suspension of crystalline or amorphous material with poor water solubility. The rate of absorption of the drug becomes dependent on the rate of dissolution of the drug, which is, in turn, dependent on the physical state of the drug, for example, the crystal size and the crystalline form. Another approach to delaying absorption of a drug is to administer the drug as a solution or suspension in oil. Injectable depot forms can also be made by forming microcapsule matrices of drugs and biodegradable polymers, such as polylactide-polyglycoside. Depending on the ratio of drug to polymer and the composition of the polymer, the rate of drug release can be controlled. Examples of other biodegradable polymers include polyorthoesters and polyanhydrides. The depot injectables can also be made by entrapping the drug in liposomes or microemulsions, which are compatible with body tissues.

Suppositories for rectal administration of the drug can be prepared by mixing the drug with a suitable non-irritating excipient, such as cocoa butter and polyethylene glycol which are solid at ordinary temperature but liquid at the rectal temperature and will, therefore, melt in the rectum and release the drug.

Solid dosage forms for oral administration may include capsules, tablets, pills, powders, gelcaps and granules. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids sucF as magnesium stearate and microcrystalline cellulose. In the case of capsules, tablets and pills, the dosage forms may also comprise buffering agents. Tablets and pills can additionally be prepared with enteric coatings and other release-controlling coatings.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferably, in a certain part of the intestinal tract, optionally in a delayed manner. Examples of embedding compositions which can be used include polymeric substances and waxes.

Dosage forms for topical or transdermal administration of a compound of this invention further include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the active compounds of this invention, excipients such as lactose, talc, silicic acid, aluminum hydroxide, calcium silicates and polyamide powder, or mixtures of these substances. Sprays can additionally contain customary propellants, such as chlorofluorohydrocarbons.

Transdermal patches have the added advantage of providing controlled delivery of active compound to the body. Such dosage forms can be made by dissolving or dispersing the compound in the proper medium. Absorption enhancers can also be used to increase the flux of the compound across the skin. The rate can be controlled by either providing a rate controlling membrane or by dispersing the compound in a polymer matrix or gel.

Accordingly, the present invention is useful in the treatment or alleviation of disease, especially those disorders related to neurological diseases or neurodegenerative disorders, such as Alzheimer's disease, Parkinson's disease, Lou Gehrig's disease, or multiple sclerosis, to name a few, not to mention central or peripheral nervous system damage, dysfunction, or complications involving same stemming from edema, injury, or trauma. Such damage, dysfunction, or complications may be characterized by an apparent neurological, neurodegenerative, physiological, psychological, or behavioral aberrations, the symptoms of which can be reduced by the administration of an effective amount of the active compounds or substances of the present invention.

According to a specific embodiment of the present invention the administration of effective amounts of anti-inflammatory agents can suppress, inhibit, or neutralize the action of increased cAMP activity, which activity if unchecked leads to the overproduction of APP. A variety of non-steroidal anti-inflammatory agents (NSAIDs) are found to be suitable for reversing the stimulatory effects of cAMP, its derivatives, a ligand, an agonist, or an antagonist of a receptor that is coupled to the cellular levels of cAMP, or a compound that enhances the nuclear actions of cAMP. Examples of suitable NSAIDs include, but are not limited to, Advil, Aspirin, Aleve, Anaprox, Diclofenac, Docosahexaenoic acid, Dolobid, Etodolac, Feldene, Flurbiprofen, Ibuprofen, Indomethacin, Ketorolac tromethamine, Lodine, Meclofenamate, 6-MNA, Motrin, Nalfon, Naprosyn, Nuprin, Orudis, Phenylbutazone, Piroxicam, Phenylbutazone, Ponstel, Relafen, Salicylic acid, Sulindac sulfide, Tolectin, Toradol, Voltaren; also 5-lipoxygenase inhibitors, phosphodiesterase inhibitors, or cyclooxygenase inhibitors (e.g., cyclosalicylazosulfapyridine or azulfasalazine).

Other suitable anti-inflammatory agents may be salicylates, such as Asacol, Disalcid, Pentesa, Salflex, or Trilisate; steroids and their combinations, such as Aerobid, Aristocort, Azmacort, Beclovent, Beconase, Celestone, Cortenema, Cortifoam, Decadron, Delalone, Depo-Medrol, Dexacort, Epifoam, Hydeltra, Hydrocortone, Hydeltrasol, Medrol, Nasacort, Plaquenil, Pediapred, Rhinocort, Solu-Cortef, Vancenase, or Vanceril; receptor-site blockers, such as leukotriene, $B_4$, $C_4$, $D_4$ and $E_4$ receptor antagonists, prostanoid receptor antagonists, prostaglandin receptor antagonists, neurokinin receptor antagonists, endothelin receptor antagonists, antihistamines, cytokine/interleukin receptor antagonists, or interferon receptor antagonist.

In a preferred embodiment of the invention the anti-inflammatory agent is selected from the group consisting of steroidal or non-steroidal anti-inflammatory agents, salicylates, steroids, receptor site blockers, or inhibitors of complement activation.

Also according to the present invention, it is contemplated that certain immunotherapeutic treatments, especially those effective to inhibit an immune or inflammatory response, can be effective in reversing, inhibiting, or otherwise, alleviating the negative effects of aberrant APP production. Such treatments include, but are not limited to, the administration of immunoglobulins or other agents for the regulation of cytokine activity, for T- and B-cell activation, for Fcg receptor blockade and for activating complement cascade; use of recombinant C3, CR1 and CR2 as inhibitors of serum complement activation; immunotoxins, immunoligands or toxin fusion proteins; the administration of vaccines or the oral administration of antigens.

Still other therapeutic "strategies" for preventing an immune or inflammatory reaction can be adopted including, but not limited to, cell/tissue transplantation, gene and stem cell therapy, adjuvant therapy, extracorporeal therapy; use of telerogenic peptides, plasmapheresis and immunoadsorption.

Immune system suppressants effective in the methods of the present invention include, but are not limited to, immunomodulators, such as Ergamisol, Leukine, Neupogen, cyclophosphamide, colony-stimulating factors and the like, and immunosuppressives, such as Atgam, Azathioprine, 15-Deoxyspergualin, HypRho, Imuran, Methotrexate, 6-Mercaptopurine, Mycophenolate mefotil (RS-61443), MICRhoGAM, Misoprostol, Methylprednisolone, Orthoclone, Prograf, Rapamycin, RhoGAM, Sandimmune, antithymocyte globulin (ATG), antilymphocyte globulin (ALG), monoclonal pan-T cell antibody (OKT3) and the like.

Neurotransmitter antagonists or modulators of signal transduction can be used to suppress the overproduction or overexpression of APP. The affected neurotransmitters include, but are not limited to adenosine, adrenoreceptors, angiotensin, atrial natriuretic peptide, bombesin, bradykinin, cholecystokinin, gastrin, dopamine, endothelin, GABA, glutamate, histamine, interleukin-1, serotonin, leukotriene, muscarinic acetylcholine, neuropeptide Y, nicotinic acetylcholine, opioid, PAF, prostanoid, purinoceptors, somatostatin, tachykinin, thrombin, vasopressin and oxytocin, VIP and the like.

Examples of modulators of kinase signaling (protein kinase A or C) include, but are not limited to phorbol esters, indolactam, mezerin, diacylglycerol, cAMP, cGMP, and their analogs; forskolin, activators or inhibitors of adenylate and guanylate cyclase; modulators of calcium or potassium channels; G-proteins; and the like.

Examples of ion-channel modulators, e.g., antagonists, that can be used according to the principles of the present invention include N-acetylprocainamide HCl, amiloride HCl, 5-(N,N-dimethyl)-amiloride HCl, 5-(N-ethyl-N-isopropyl)-amiloride, 5-(N,N-hexamethylene)-amiloride, 5-(N-methyl-N-isobutyl)-amiloride, 4-aminopyridine, amiodarone HCl, apamin, R(+)-Bay K 8644, benzamil HCl, bepridil HCl, β-bungarotoxin, 2,3-butanedione monoxime, calciseptine, charybdotoxin, μ-conotoxin GIIIA, ω-conotoxin GVIA, ω-conotoxin MVIIC, cyclic ADP ribose (cyclic ADPR), cyclopiazonic acid, cyproheptadine HCl, dantrolene sodium salt, dendrotoxin, R(+)-DIOA, diltiazem HCl, efaroxan HCl, flunarizine HCl, fluspirilene, glibenclamide, glipizide, HA-1077 2HCl, 5-hydroxydecanoic acid sodium salt, IAA-94, iberiotoxin, kaliotoxin, lidocaine N-ethyl bromide (QX-314), loperamide HCl, manoalide, MCD peptide, NAADP, nicardipine HCl, nifedipine, nifedipine metabolite, (±)-niguldipine HCl, S(+)-niguldipine HCl, R(−)-niguldipine HCl, nimodipine, nitrendipine, 5-nitro-2-(3-phenylpropylamino)benzoic acid (NPPB), phenamil methanesulfonate, N-Phenylanthranilic acid, phentolamine mesylate, pimozide, procainamide HCl, quinidine sulfate, quinine sulfate, ruthenium red, ryanodine, saxitoxin, tetraethylammonium chloride, tetrodotoxin, tetrodotoxin citrate, thapsigargin, tityustoxin-Kα, TMB-8 HCl, tolbutamide, triamterene, (±)-verapamil HCl, S(−)-verapamil HCl, R(+)-verapamil HCl, normethyl verapamil, (+)-methoxy-verapamil HCl, S(−)-methoxy-verapamil HCl, R(+)-methoxy-verapamil, and YS-035 HCl. These and related compounds can be obtained commercially, such as from Research Biochemicals International.

The following examples are provided for further illustration of the present invention, and do not limit the invention.

6. EXAMPLES

Experiments and exemplary procedures are described below which provide additional enabling support for the present invention. In particular, in vitro studies using primary cultures of rat cortical astrocytes and in vivo studies using appropriate animal models are disclosed.

6.1. General Methods

Astrocytes are isolated from cortices from postnatal rats. See, K. D. McCarthy and J. de Vellis, J. *Cell Biol.* 85, 890 (1980). In brief, dissected cortices were dissociated by trypsinization and trituration through a flame-polished Pasteur pipette. Cells were plated onto poly-L-lysine coated 35- or 100 mm culture dishes at densities of about 10–25 cells/$mm^2$. The initial culture media, minimal essential medium (MEM, Gibco) containing 10% horse serum (BioWhittaker), were aspirated after 2–5 h after plating to remove unattached cells and debris, and replaced with MEM containing 7.5% fetal bovine serum (FBS, BioWhittaker). Half the media was replaced with MEM/7.5% FBS twice weekly. Cells are kept at 37° C. in a humidified 5% $CO_2$/ 95% air incubator. Media are changed twice weekly. Immunocytochemical staining with antibodies against GFAP and tau shows that >90% of cultured cells are astrocytes and <5% are neurons. Pharmacological manipulations are performed in serum-free media on 7–14 DIV confluent astrocytes.

6.2. Detection of Cell-Associated Protein

To detect cell-associated protein (APP or GFAP), astrocytes from 35 mm dishes are scraped in lysis buffer (60 mM Tris/HCl, 4% SDS, 20% glycerol, 1 mM dithiothreitol), ultrasonicated and boiled for 5 min. The total amount of cell protein per dish, estimated using the bicinchoninic acid assay, is not altered by pharmacological treatments. Bromphenol blue (0.1%) is added to each sample and equal amounts of protein (~75 mg/lane) are loaded on 10% SDS-polyacrylamide gels.

To detect secreted APP, culture media was collected after drug treatments and phenylmethylsulfonyl fluoride was added to a final concentration of 2mM. The media samples were then applied to Sephadex PD-10 desalting columns (Pharmacia) and eluted with distilled water. Column eluates were frozen and dried by vacuum centrifugation. The lyophilized proteins were reconstituted in 25 μL water followed by 25 μL of 2× Laemmli gel loading buffer, and boiled for 5 min.

The amount of media or cell protein loaded for sodium dodecyl sulfate-polyacrylamide gel electrophoresis (10–20% SDS PAGE; Bio-Rad) was normalized for the amount of protein per sample. Proteins (equivalent to ~100 μg cell protein/lane) were seperated by electrophoresis, electroblotted onto polyvinylidene difluoride membranes (Immobilon-P, Millipore) and blocked in Tris-buffered saline with 0.15% Tween 20 (TBST) containing 5% powdered milk for 30 min. After 2×10 min rinses in TBST, the membranes were incubated in TBST containing an appropriate antibody. Monoclonal antibodies 22C11 and GFAP (both from Boehringer-Mannheim) were used to detect the N-terminus of APP and glial fibrillary acidic protein respectively; antisera R37 and R98 (gifts of Dr. F. Kametani, Tokyo Institute of Psychiatry) were used to detected the C-terminus and KPI motifs of APP respectively; antiserum C8 (gift of Dr. D. Selkoe, Women's Hospital, Harvard Medical School, Cambridge, Mass.) was used to detect the C-terminus of APP.

After an overnight incubation, membranes were rinsed in TBST before being treated for 1 h with a peroxidase-linked secondary antibody. After several rinses in TBST, protein bands were visualized on Kodak X-AR films by an enhanced chemiluminescence method (Amersham). Optical densities of the protein bands were quantitated by laser scanning densitometry (LKB, Bromma, Sweden), and normalized to the densities of those bands generated under control conditions.

6.3. cAMP Assay

Levels of cyclic AMP were measured with [8-$^3$H]-cAMP assay kit (Amersham TRK 432) in astrocytes grown on 35 mm dishes. In brief, after aspirating the medium and rinsing twice with 1 ml ice cold PBS, the cells were scraped in 0.8 ml ice cold ethanol and sonicated. The cell suspension was incubated for 5 min at room temperature, centrifuged and the supernatant was dried in a rotary evaporator. After resuspension in 120 μl Tris/EDTA buffer, two duplicate samples of 50 μl each were mixed with the binding protein, [8-$^3$H] adenosine 3', 5'-cyclic phosphate tracer and incubated at 2–4° C. for 2 h. A charcoal suspension (100 μl) was added to the samples before centrifugation and 200 μl of the supernatant were removed for scintillation counting. The amount of cyclic AMP (pmol/mg protein) was estimated by comparing to known standards, and normalized to the amounts of whole cell protein as determined by the bicinchoninic acid assay (Sigma).

6.4. Data Analysis

Measurements of cellular and secreted proteins, or of mRNA in treatment groups were normalized against those of control groups which were prepared in parallel and loaded onto the same blot. Analysis of variance (ANOVA) and t-tests were used to evaluate differences between groups (significance level, p=0.05), using drug treatments as the independent variable.

6.5. Analysis of RNA

Total RNA from astrocytes grown on 100 mm dishes is extracted by the acid guanidium thiocyanate-phenol-chloroform method. See, P. Chomcznski and N. Saachi, *Anal. Biochem.* 162, 156 (1987). In brief, the medium was aspirated and the cells were scraped in 1 mL of TRI Reagent. After incubation for 15 min at room temperature, 0.2 ml chloroform was added, mixed vigorously with TRI Reagent and the mixture was stored for another 15 min at room temperature. After centrifugation at 12,000 g for 15 min, 0.5 ml isopropanol was added to the aqueous phase of the mixture to precipitate RNA. The RNA pellet collected by centrifugation (12,000 g, 15 min at 4° C.) was washed with 70 % ethanol once and solubilized in an appropriate amount of Formazol (Molecular Research Center, Cincinnati, Ohio). RNA samples (~20 μg) were denatured by heating for 15 min at 60° C. prior to loading onto 1.2% agarose-formaldehyde gels for electrophoresis. RNA was blotted onto Hybond polyvinyl membranes by overnight capillary transfer and fixed onto the membranes by UV light illumination. Membranes were pre-hybridized with Amersham Rapid-hyb (Amersham Lab, Arlington Heights, Ill.) buffer for 2 h and labeled overnight with a ~1.8 kb human APP cDNA (gift of Dr. Rachael Neve, McLean Hospital, Harvard Medical School, Belmont, Mass.) or human glyceraldehyde-3-phosphate dehydrogenase probe (G3PDH; Clontech) labelled with [32p]dCTP using random primed extension (Amersham Megaprime DNA labelling kit). Membranes were dried and exposed to Kodak X-ray film for 24–48 h with an Amersham enhancer sheet. The relative amounts of mRNA obtained by hybridization were estimated using densitometric analysis of autoradiographs. The levels of APP mRNA were normalized to the amounts of G3PDH mRNA and expressed as a ratio to the levels of untreated, control cells.

6.6. Exposure of Astrocytes to cAMP, NE and Others

Confluent monolayers of astrocytes prepared according to Example 5.1 and treated with serum-free media containing 50, 100, or 250 μM 8Br-cAMP for varying durations (1 h, 6 h, 12 h, or 24 h). Levels of cAMP in astrocytes are measured with a [8-$^3$H]-cAMP assay kit (Amersham TRK 432).

Cultures of astrocytes are also treated with norepinephrine (NE, 50 and 100 μM) or with NE plus propranolol (50 μM). Cells are also exposed to NE (50 μM) or to the β-adrenergic agonist isoproterenol (50 μM) to stimulate APP mRNA synthesis. The effects of other substances, including PMA, DNF, 8Br-cAMP, forskolin, prostaglandin $E_2$, H8, H9, Win55212, Sp-cAMPS triethylamine and cyclosporin A are also observed, similarly.

Assays of PI hydrolysis are conducted as previously reported. Also, measurements of APPs are conducted as previously reported.

6.7. In Vivo Studies

The present studies indicate that immune system suppressants, such as cyclosporin A, can inhibit APP overexpression in GFAP-immunoreactive cultured astrocytes. Reactive astrocytes (that is, astrocytes that have been activated or stimulated in some fashion, e.g., those associated with brain or neuronal injury) in vivo also upregulate GFAP expression. Indeed, the examination of post-mortem brains in patients with Alzheimer's disease shows that reactive astrocytes are found in proximity to amyloid plaques and regions of neurodegeneration. The inventors believe that neuronal, brain, or head injury gives rise to the formation of reactive astrocytes, which overexpress APP and contribute to the formation of amyloid or neurotoxic APP derivatives.

Thus, animal models of head injury and Alzheimer's disease exhibit increased amounts of APP in the brain. The in vivo administration of immune system suppressants, like cyclosporin A, is found to inhibit APP overexpression and the associated neurological disorders. Inasmuch as head injury is associated with Alzheimer's disease (e.g., boxers with dementia pugilists), treatment with immunosuppressants may prevent the progression of neuropathological symptoms associated with this disease. Likewise, it is found that the in vivo administration of agents that reduce or prevent astrocytic inflammation (e.g., reactive astrogliosis) reduces GFAP immunoreactivity and APP overexpression.

7. RESULTS

In summary, confluent primary rat cortical astrocytes, which are treated with serum-free medium containing 50, 100, or 250 μM, respectively, of 8-Bromo-cAMP (8Br-cAMP) for 24 h, show a dose-dependent increase in APP mRNA on Northern blots (120%, 150% and 180% of untreated cells). In comparison, β-actin mRNA is decreased to 50% of untreated cells by 8Br-cAMP (250 μM). Both L-norepinephrine (NE, 50 or 100 μM) and the β-adrenergic agonist isoproterenol (50 μM) increase APP mRNA to 180% of untreated cells. The β-adrenergic antagonist propranolol (50 μM) reduces the NE-stimulated increase in APP mRNA to baseline levels. N- and C-terminal APP antibodies 22C11 and R37 (from Dr. F. Kametani, Tokyo Inst. Psychiatry), respectively, show that 8Br-cAMP or NE also increases APP holoprotein in cell lysates to 200% of that seen in untreated cells. Both drugs also increase process formation and glial fibrillary acidic protein immunoreactivity in astrocytes. Thus, activation of β-adrenergic receptors coupled to cAMP formation increases both APP mRNA and holoprotein in reactive astrocytes.

The APP gene promoter contains a consensus sequence for a cAMP response element (CRE). The immunosuppressant cyclosporin A (CycA, 10 μM), which is known to inhibit CRE-mediated transcription, blocks the increase in APP protein caused by 8Br-cAMP. This result suggests that CycA may be used to prevent increases in APP and, potentially, amyloid formation in neurodegenerative diseases, such as Alzheimer's disease.

More specifically, and referring now to FIG. 1, confluent monolayers of astrocytes are incubated for 24 h in serum-free media containing 50, 100, or 250 μM 8Br-cAMP. A, Representative immunoblot with mAb22C11 shows that astrocytes incubated with NE (50 μM) contain significantly more cell-associated APP relative to untreated control cells, Con ($p<0.05$), and that this increase is inhibited by the β-adrenergic antagonist propranolol (Prop, 50 μM). This experiment is replicated with similar results. B, Representative Northern blot indicates that two doses of NE (50 or 100 μM) are equally effective in stimulating an increase in APP mRNA levels above those of controls (Con), and that this effect is mimicked by the β-adrenergic agonist isoproterenol (Iso, 50 μM). G3PDH mRNA is used as a control for RNA loading and is not affected by drug treatments. C, The stimulatory effect of NE or isoproterenol on APP mRNA synthesis (*, $p<0.05$) is significantly inhibited by the β-adrenergic antagonist propranolol.

Figure 2:
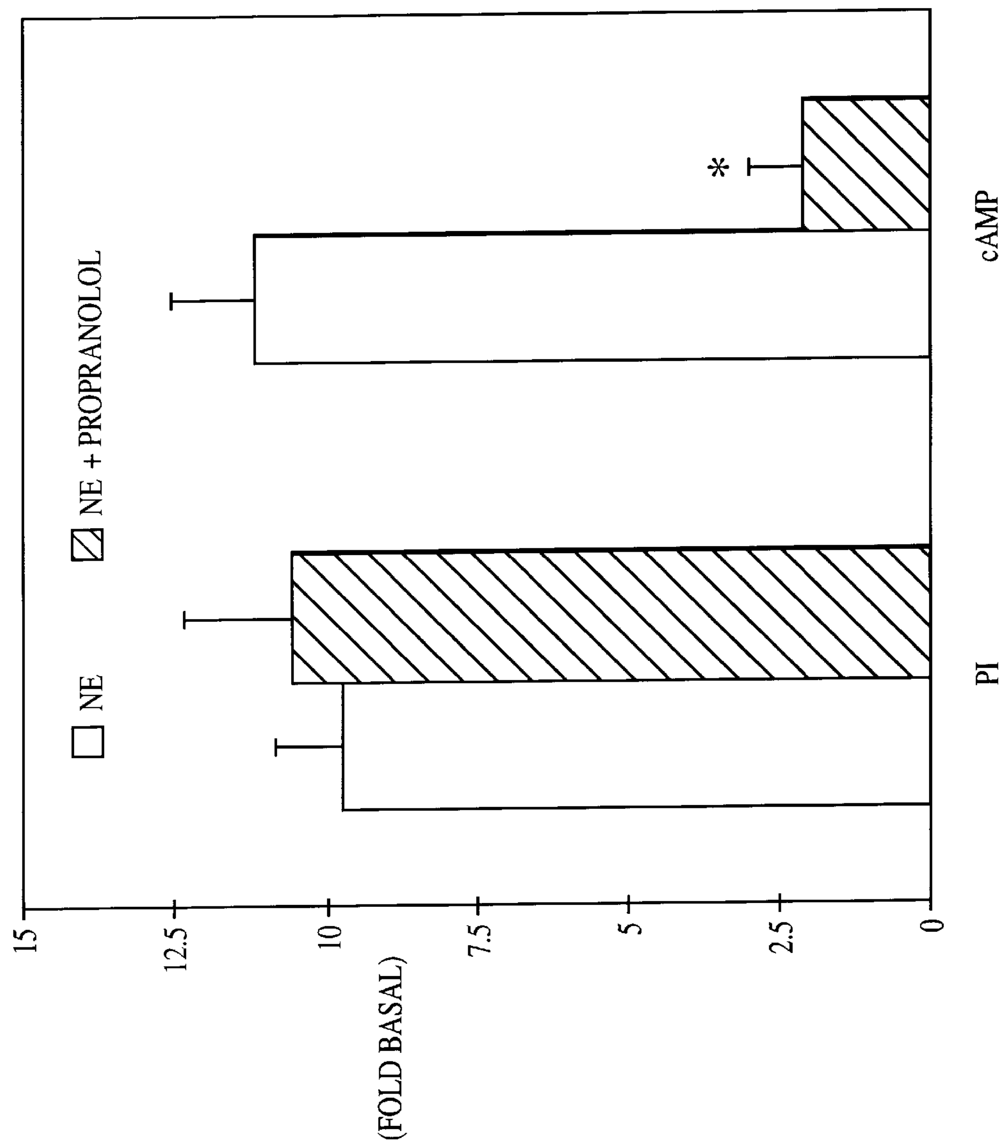
FIG. 2 illustrates the effect of propranolol on the changes in PI hydrolysis and cAMP formation caused by NE treatment.

Referring now to FIG. 2, PI hydrolysis and cAMP formation are significantly increased by 1 h treatment with NE (50 μM). Co-incubation with propranolol (50 μM) inhibits the increase in cAMP formation caused by NE (*, $p<0.05$) but has no effect on the increase in PI hydrolysis. Graphs represent means and SEM that are obtained from three independent experiments.

Referring now to FIG. 3, A is a representative immunoblot that shows that phorbol 12-myristate 13-acetate PMA (5 μM) or dexnorfenfluramine hydrochloride DNF (100 μM) treatment of astrocytes prepared according to Example 5.1 for 1 hour significantly increases APPs secretion relative to untreated cells (Con). B, indicates that these same drugs have no effect on the amount of cell-associated APP (APP holoprotein) after 24 hours. APP is detected by mAb22C11 on both immunoblots. Three experiments produce similar results.

Figure 4A:
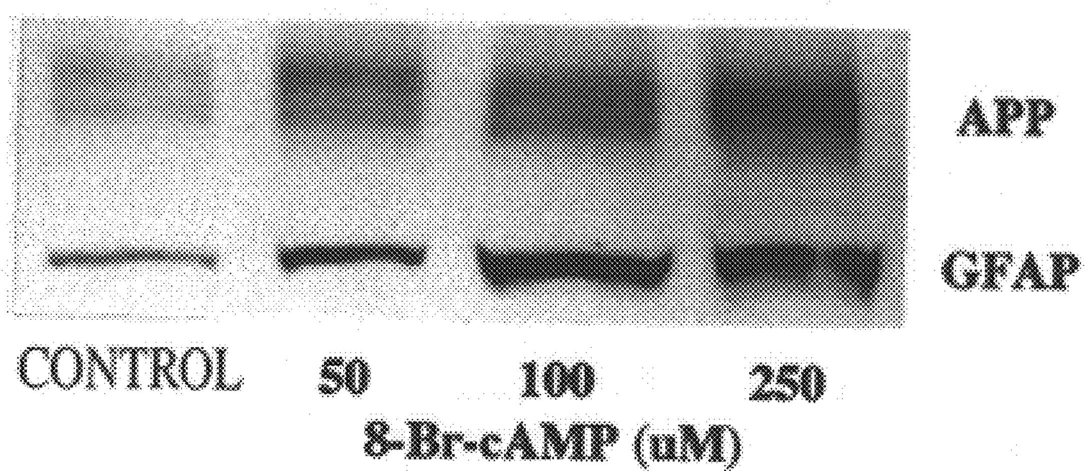
FIGS. 4A and 4B illustrate the effects of 8Br-cAMP and forskolin on cell-associated APP and GFAP from cultured astrocytes.
Figure 4B:
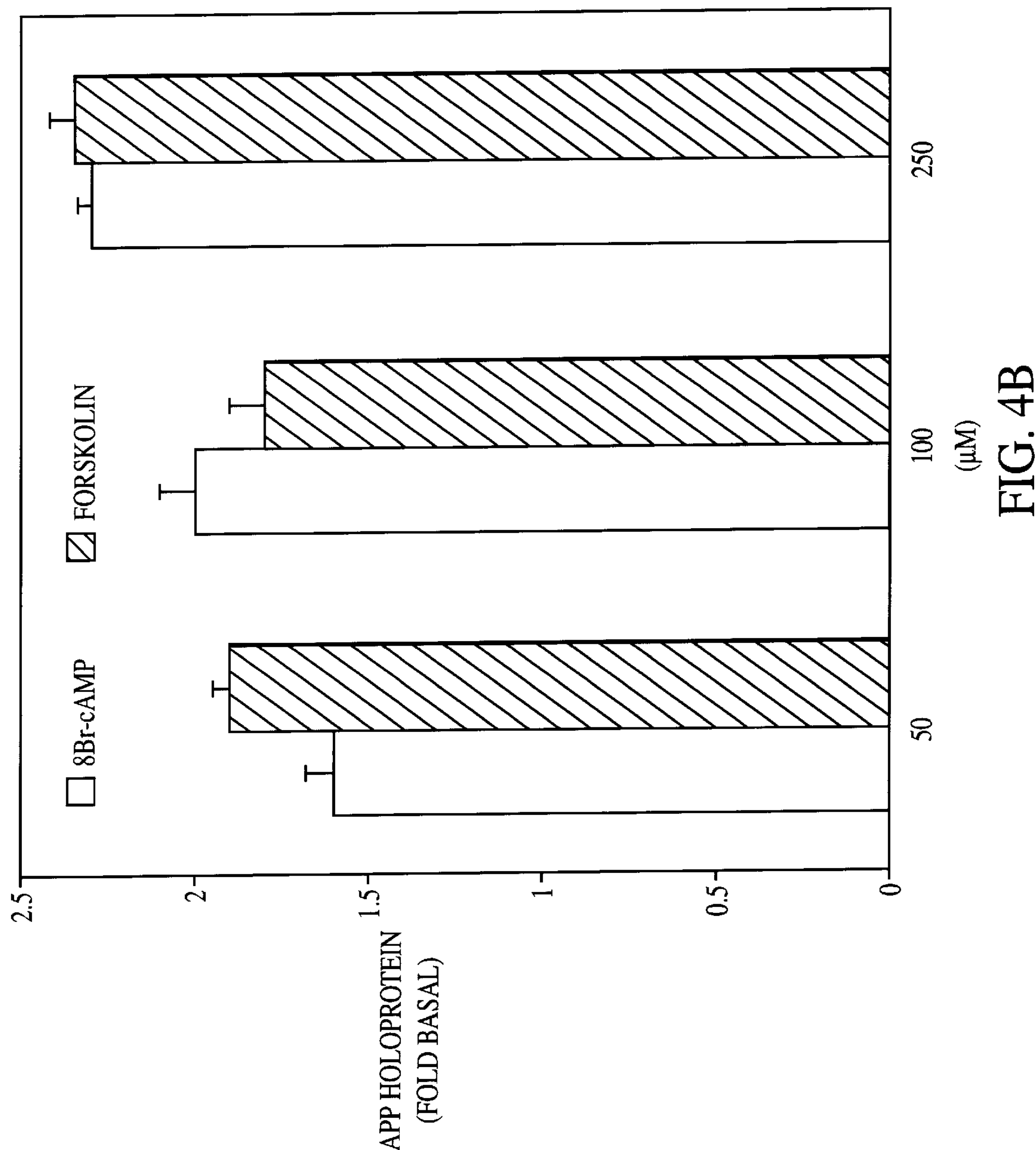

Confluent astrocytes are prepared as in Example 5.1. The cells are scraped and suspended in SDS-reducing sample buffer for loading on Western blots. Referring now to FIG. 4, A is a representative immunoblot in which R37 antiserum and GFAP monoclonal antibody reveals two protein bands at ~120 kD (APP) and ~50 kD (GFAP), respectively. B, charts the results of 24 h exposure of the cells to increasing concentrations of the cAMP analog, 8Br-cAMP, or forskolin (50, 100 or 250 μM). As detected by antiserum R37 or mAb22C11, the amounts of cell-associated APP increases with increasing concentrations of both drugs (*, $p<0.05$). The graph presents data accumulated from 3 independent experiments.

Referring now to FIG. 5, APPs in the media is detected as a ~110 kD protein by mAb22C1l. A, a representative immunoblot, shows that treatment with 250 μM 8Br-cAMP for ca. 1 hour suppresses APPs secretion. Greater amounts of APPs accumulates in the medium after 24 hour exposure to 8Br-cAMP versus 1 hour. B, the graph shows that APPs is statistically significantly reduced (*, $p<0.05$) after about 1 hour of exposure to 8Br-cAMP, with the opposite trend after about 24 hour exposure. The graph represents the mean and SEM from three independent experiments.

Referring now to FIG. 6, astrocytes prepared as in Example 5.1 are used. A representative Northern blot indicates an increase in APP mRNA with increasing concentrations of 8Br-cAMP. The G3PDH mRNA is unaffected by 8Br-cAMP treatments. Subsequent experiments show that 250 μM is the most effective and reliable 8Br-cAMP concentration for stimulating APP synthesis.

Turning now to FIG. 7, the usual astrocytes are incubated with 8Br-cAMP (250 μM) or NE (50 μM) for about 24 hours. A representative Northern blot shows that both drug treatments increase APP mRNA and decrease β-actin mRNA levels. Three independent experiments produce similar effects.

As before, astrocytes prepared according to Example 5.1 are treated with increasing concentrations of 8Br-cAMP or forskolin for 24 hours. As shown in the graph of FIG. 8, 8Br-cAMP and forskolin (both at 50, 100, or 250 μM) cause significant increases in GFAP protein, as assayed using Western blots (*, $p<0.05$) The graph represents the mean and SEM obtained from 3 independent experiments.

In FIG. 9, A is a representative immunoblot showing that the increase in cell-associated APP caused by 24 hour treatment with 8Br-cAMP (250 μM) is suppressed by co-treatment with 1 μM cyclosporin A. This immunoblot also shows that cyclosporin A alone has no effect on the basal APP levels. B, a representative immunoblot showing that basal APPs secretion levels are unaffected by 24 hour treatment with 8Br-cAMP, with or without 1 μM cyclosporin A. C, graphically shows how the suppression of the 8Br-cAMP-induced increase in cell-associated APP is not significantly different at three doses of cyclosporin A (1, 5, or 10 μM). The graph represents the mean and SEM of pooled data obtained from 3 independent experiments.

It is also observed that the modulation of immune and/or inflammatory responses, which is achieved by the administration of immunosuppressants and/or anti-inflammatory agents, e.g., cyclosporin A, FK-506 and cannabinoid compounds; see, e.g., R. Condie, A. Herring, W. S. Koh, M. Lee, N. E. Kaminski, J. Biol. Chem., 271, 13175 (1996), in turn prevents or inhibits APP overexpression.

PG $E_2$ coupled to cAMP production increases the expression of APP holoprotein and mRNA.

Figure 10A:
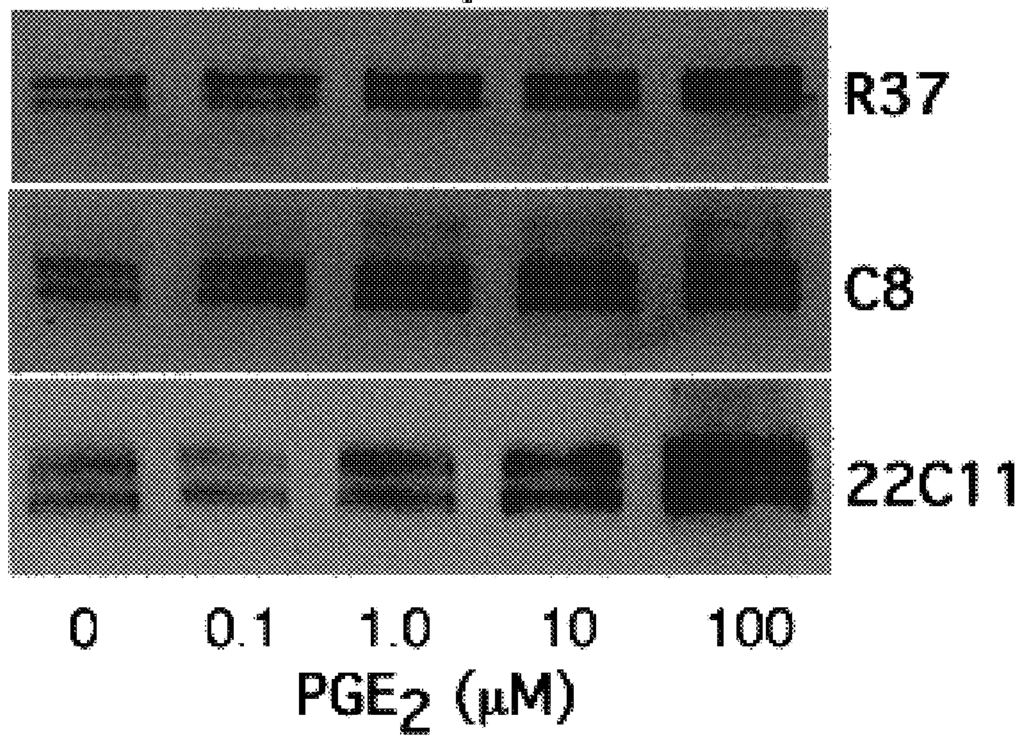
FIGS. 10A, 10B, 10C and 10D illustrate the effects of PG $E_2$ in increasing cellular levels of APP holoprotein, levels of secreted APP, and cellular cAMP levels.
Figure 10B:
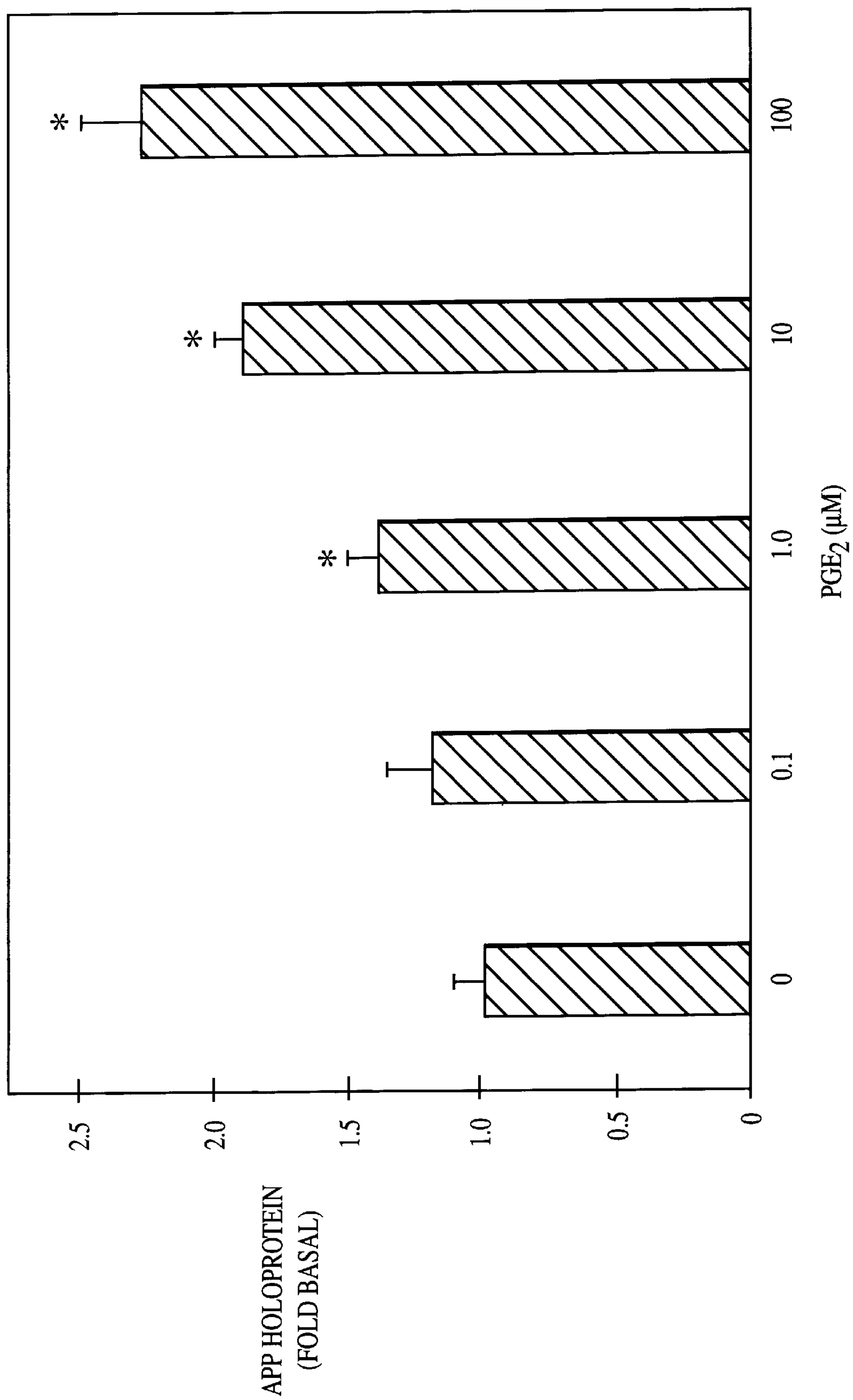

Treatment of astrocytes for 24 h with 1, 10 or 100 μM PG $E_2$ significantly increased the amounts of astrocytic APP mRNA (~4.5 kb) relative to untreated cells (all p<0.05) (FIG. 10A). Similar increases in APP holoprotein (~110–130 kD) were detected by mAb 22C11, antisera R37 or R98 on Western blots. Treatment with 1, 10 or 100 μm PG $E_2$ produced increases in cellular APP holoprotein that were 1.4, 1.9 and 2.3-fold respectively of untreated, control cells (FIG. 10B).

Figure 10C:
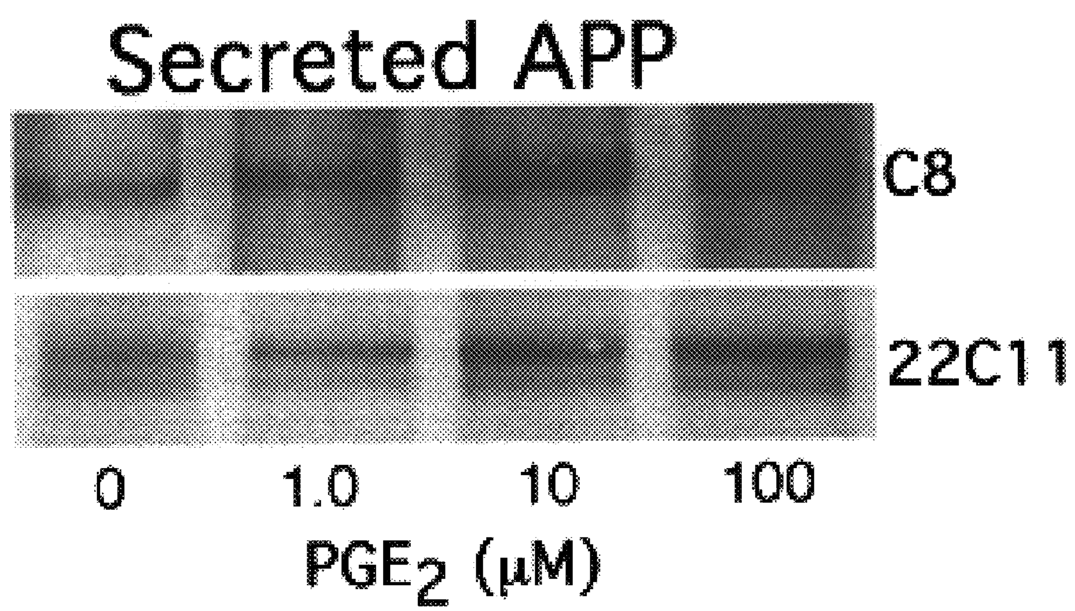
Figure 10D:
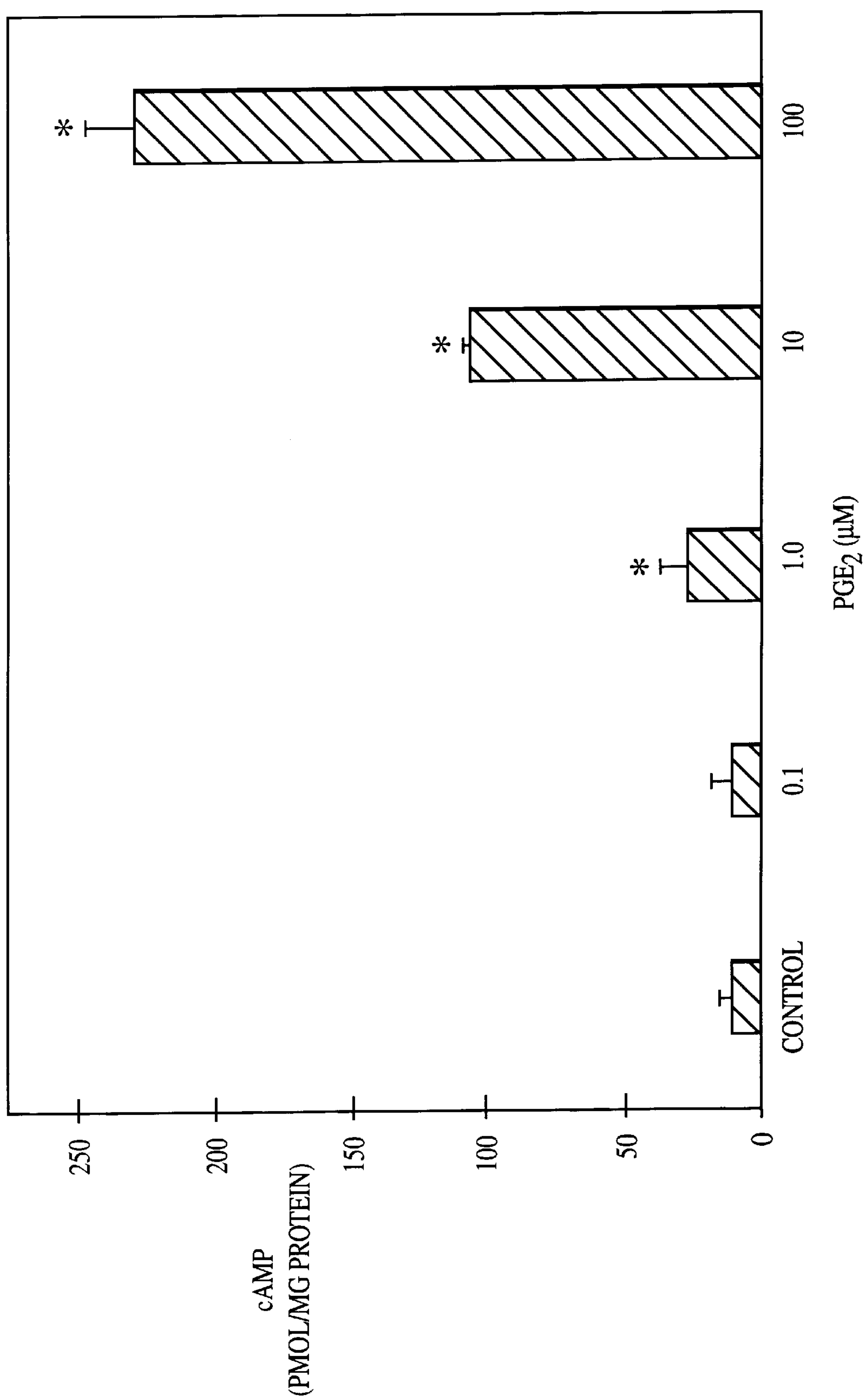

APP secreted in the media (~110–130 kD) was also increased by 24 h treatment with 1, 10 or 100 μM PG $E_2$ using mAb 22C11, antiserum R37 or C8 immunodetection (FIG. 10C). Treatment with 1, 10 or 100 μM PG $E_2$ also stimulated dose-dependent increases in cellular cAMP levels to 27, 106 and 227-fold compared to that of untreated cells (FIG. 10D); 0.1 μM PG $E_2$ did not stimulate cAMP production, and did not significantly alter APP holoprotein or mRNA levels compared to untreated, control astrocytes (p>0.05).

Protein kinase A and cAMP regulate APP expression.

Figure 11A:
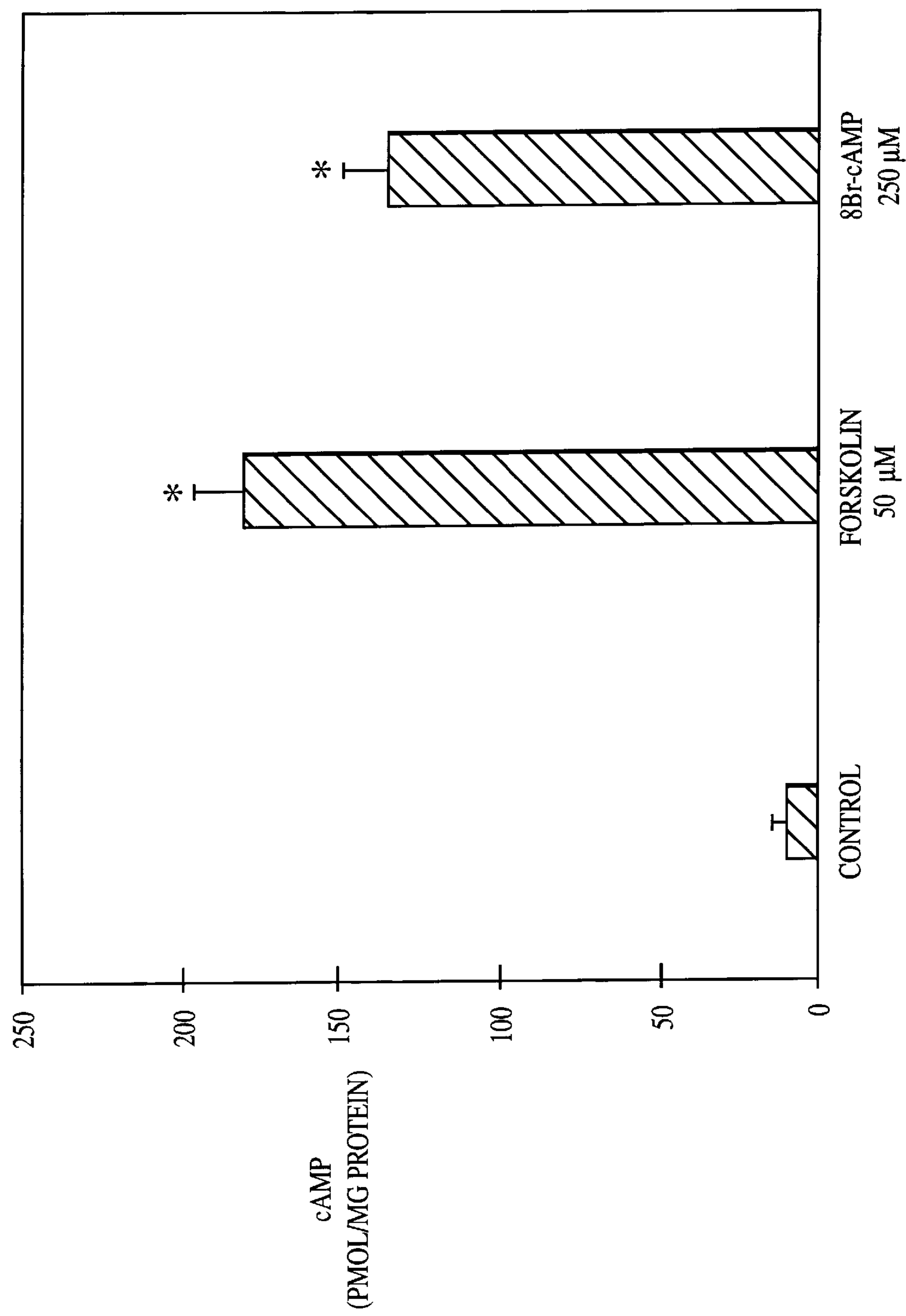
FIGS. 11A and 11B illustrate the effects of 8Br-cAMP and forskolin on cellular cAMP levels, and on levels of APP mRNA, APP holoprotein, and GFAP.
Figure 11B:
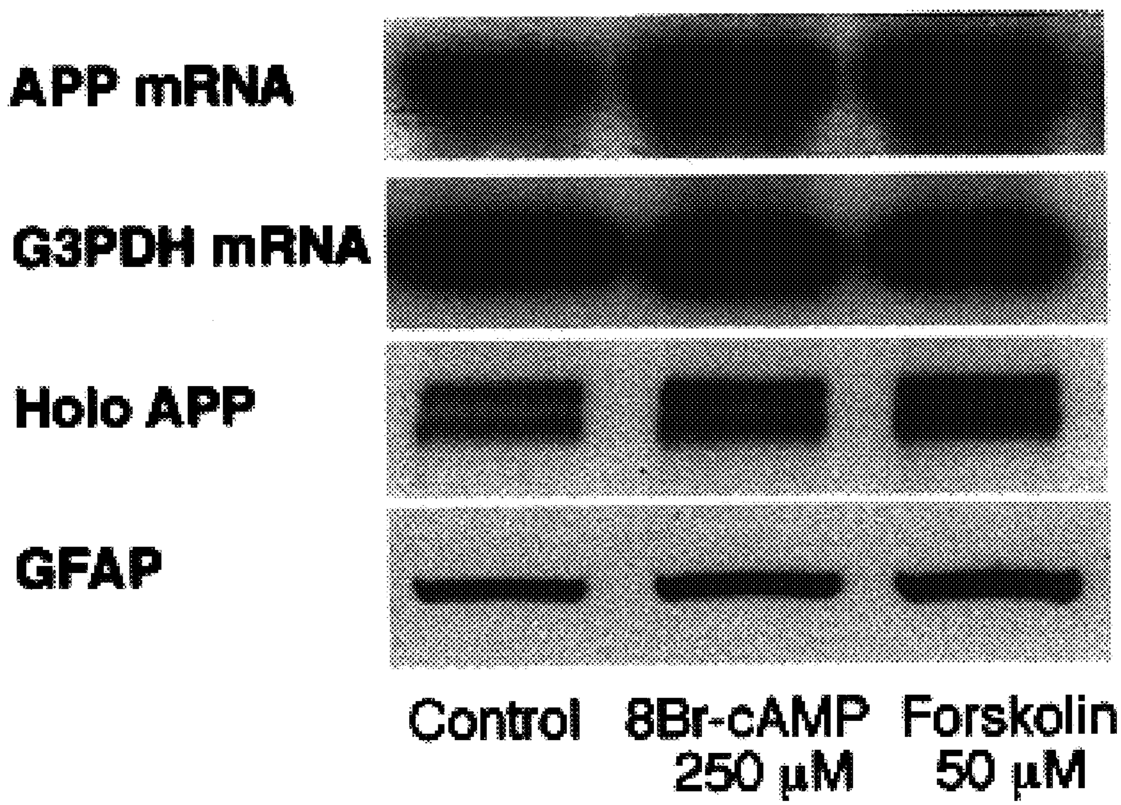

Treatment of astrocytes for 1 h with membrane-permeant 8Br-cAMP (250 μM) or by activating adenylate cyclase with forskolin (10, 50 or 100 μM) significantly increased cellular cAMP levels (FIG. 11A), and similar increases in APP mRNA and holoprotein (FIG. 11B).

Figure 12A:
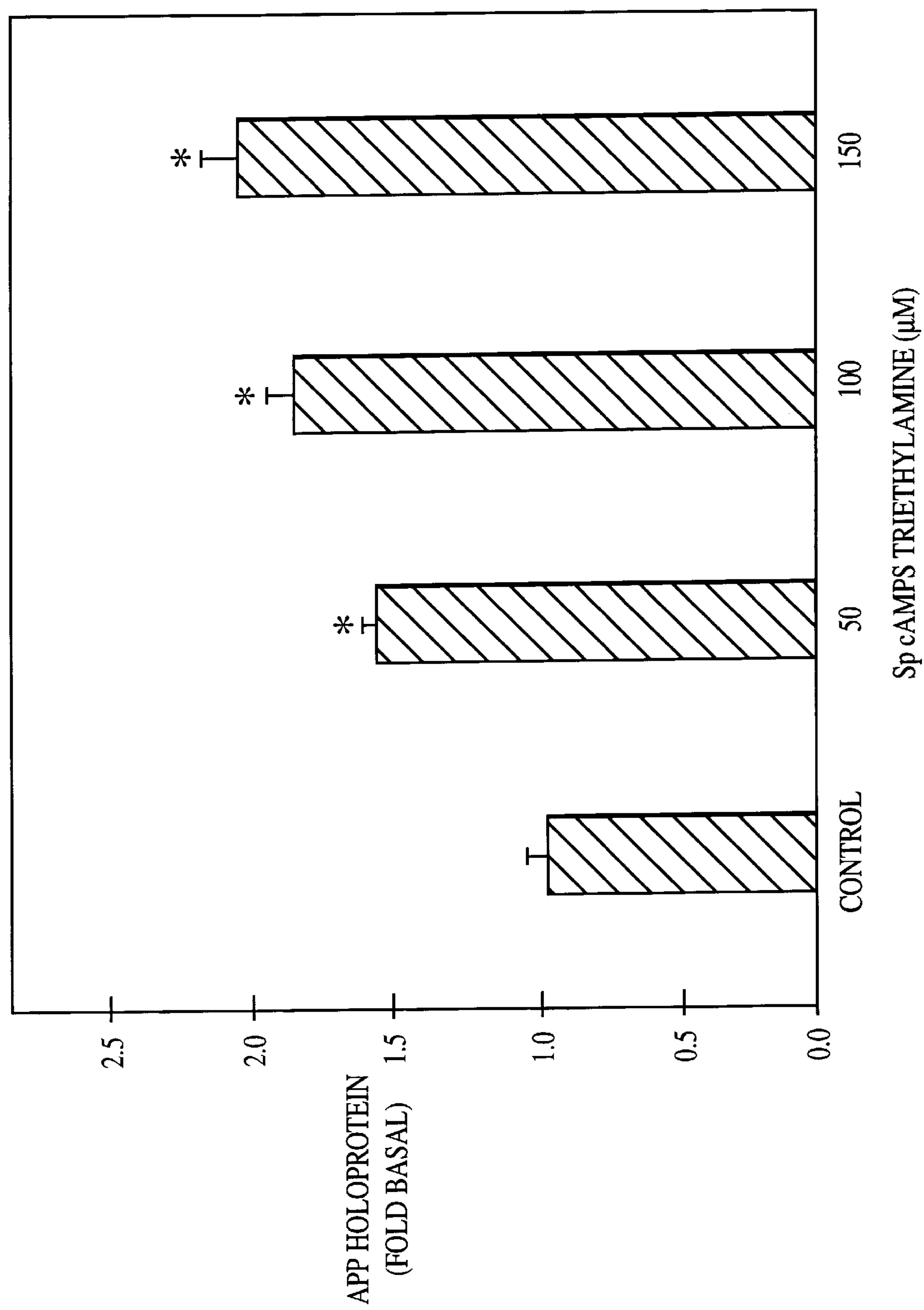
FIGS. 12A and 12B illustrate the effects of Sp-cAMPS triethylamine on APP holoprotein levels, and the effects of the PKA inhibitor H-89 on APP mRNA and APP holoprotein stimulated by PG $E_2$.
Figure 12B:
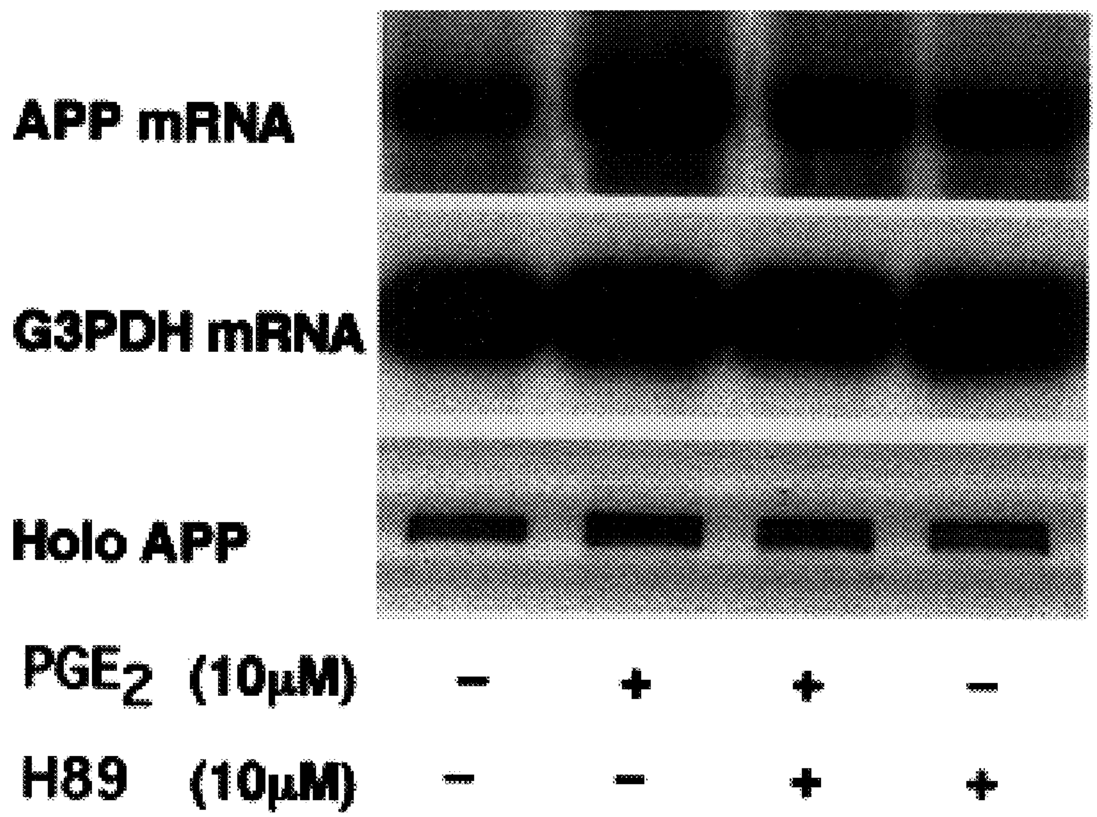

Activation of protein kinase A by 24 h treatment with 50, 100 or 150 μM Sp-cAMP triethylamine increased cellular levels of APP holoprotein to 1.6, 1.9 and 2.2-fold compared to untreated cells (FIG. 12A). By contrast, inhibition of protein kinase A with 100 μm of PKA inhibitor H-89 completely abolished the increase in APP holoprotein stimulated by 24 h treatment with 10 μM PG $E_2$ (FIG. 12B) APP was detected with antiserum R98 directed at the KPI motif of APP. These results were replicated in subsequent experiments using mAb 22C11 or R37 directed at the N- and C-termini of APP respectively.

Immunosuppressants cyclosporin A or FK-506 inhibit APP synthesis stimulated by PG $E_2$ or cAMP elevations.

Figure 13A:
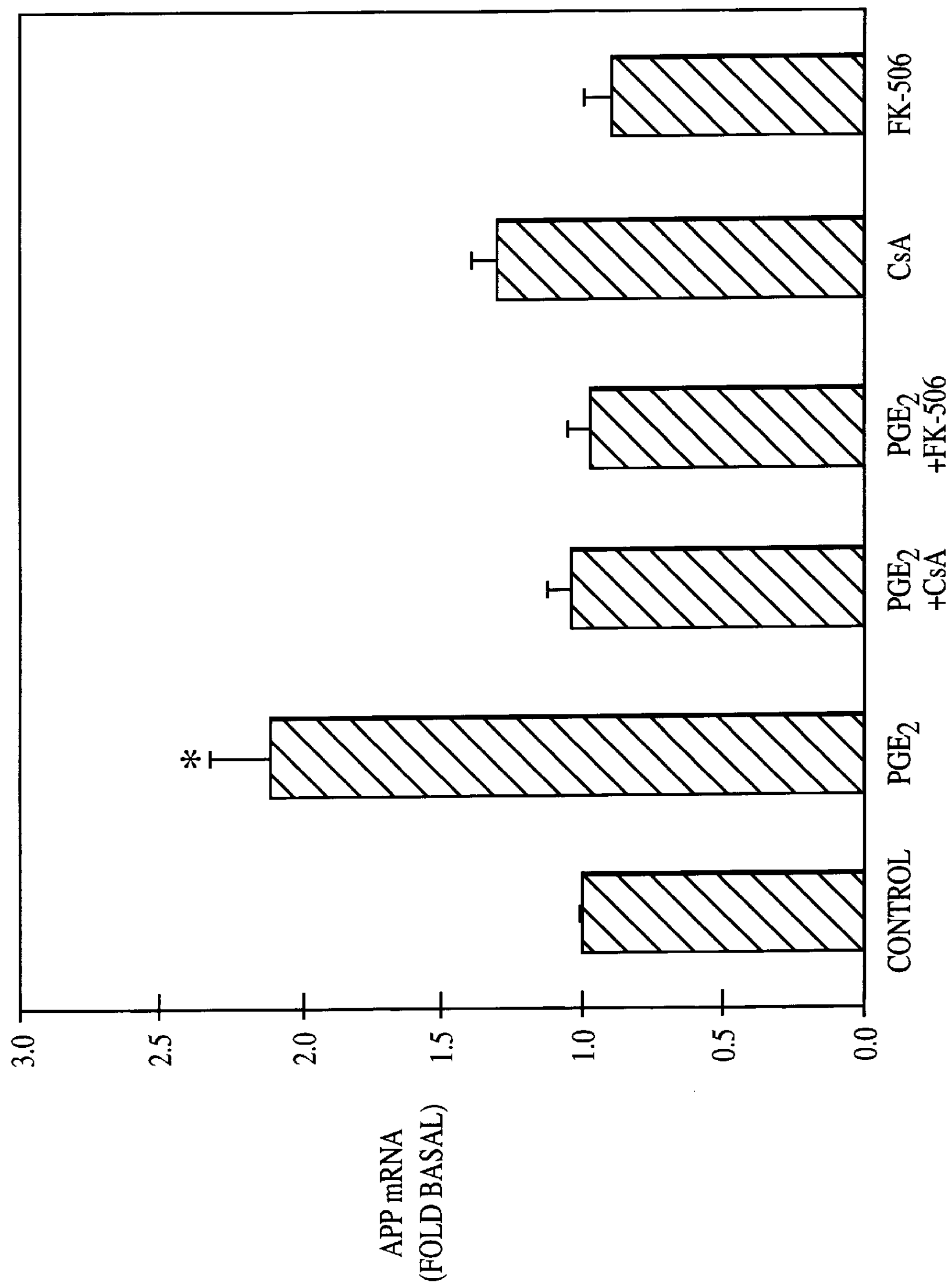
FIGS. 13A, 13B and 13C illustrate the effects of cyclosporin A or FK-506 on increases in APP mRNA, APP holoprotein, and GFAP levels stimulated by PG $E_2$ or forskolin.
Figure 13B:
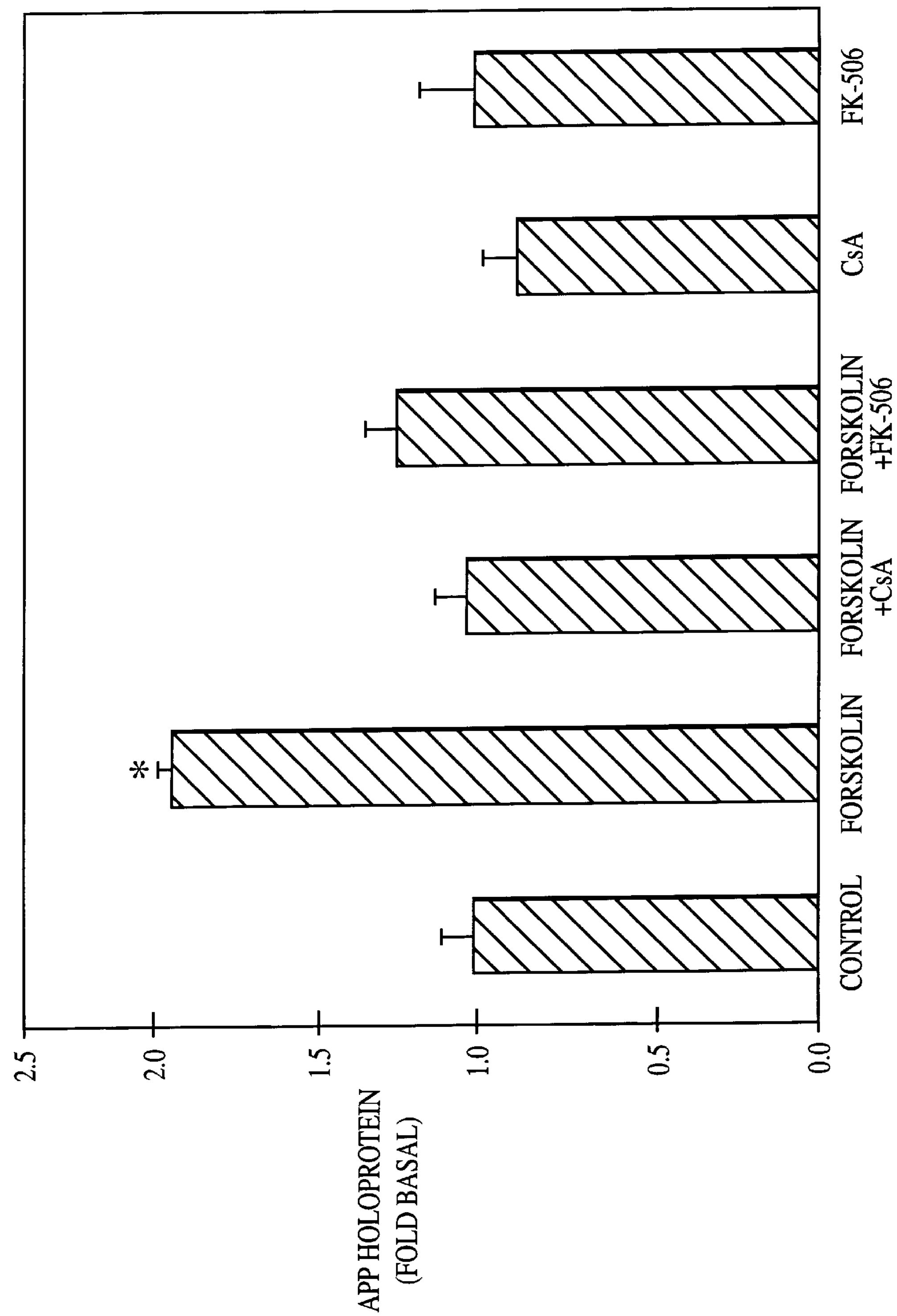
Figure 13C:
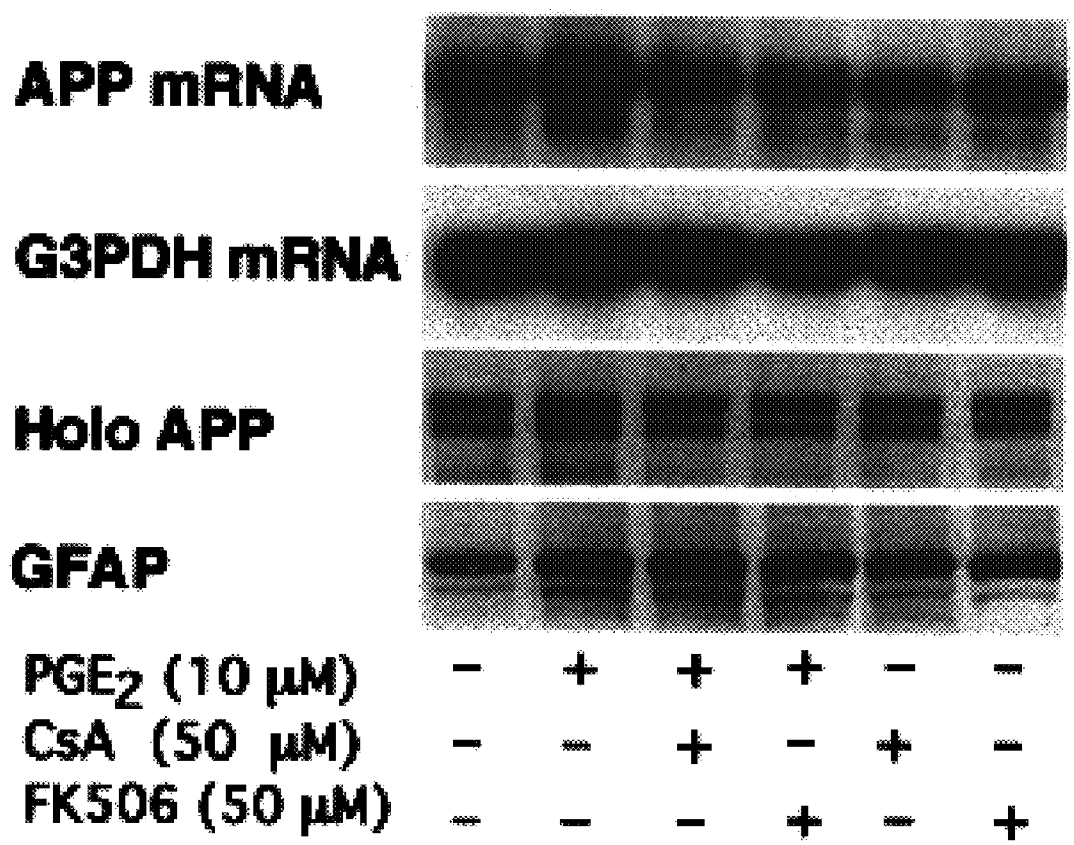
Figure 14:
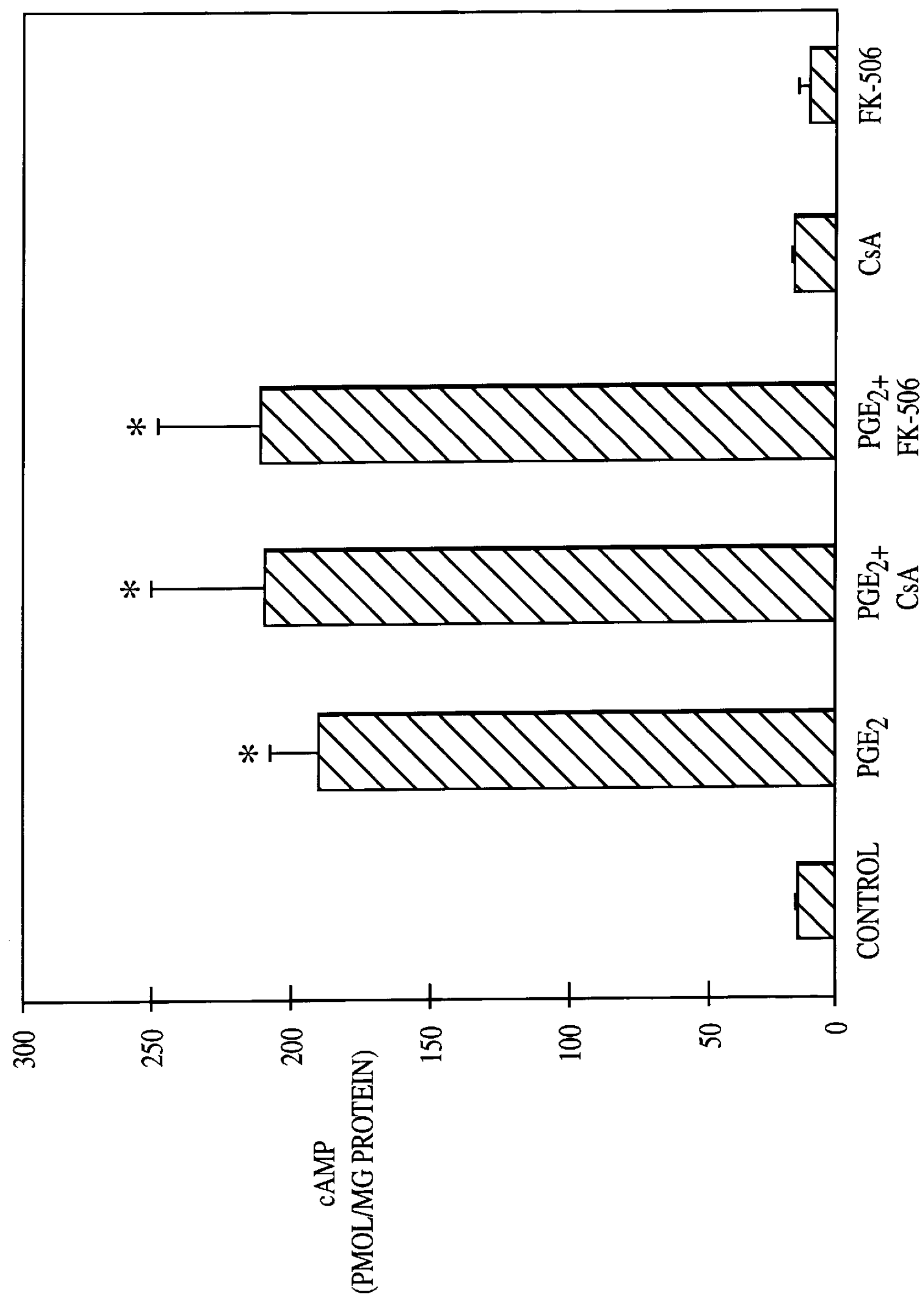
FIG. 14 illustrates the effects of cyclosporin A and FK-506 on cellular cAMP levels stimulated by PG $E_2$.

The increases in astrocytic APP holoprotein and mRNA stimulated by 24 h treatments with 50 μm forskolin or 10 μM PG $E_2$ were significantly inhibited by co-treatment with either 50 μM cyclosporin A or 50 μM FK-506 (FIG. 13). Representative Northern and Western blots show that the increases in APP mRNA and APP holoprotein, but not the increases in GFAP levels, stimulated by PG $E_2$ (10 μM) are inhibited by cyclosporin A (CsA) or FK-506 (both 50 μM). Also, neither cyclosporin A nor FK-506 had a significant effect on cellular cAMP levels stimulated by 10 μM PG $E_2$ (FIG. 14). Treatment of astrocytes with either cyclosporin A or FK-506 (both 50 μM) alone had no significant effect on basal APP holoprotein or cAMP levels (p>0.05)

Nicotinic ditartrate coupled to cAMP production increases the expression of APP holoprotein.

Figure 15A:
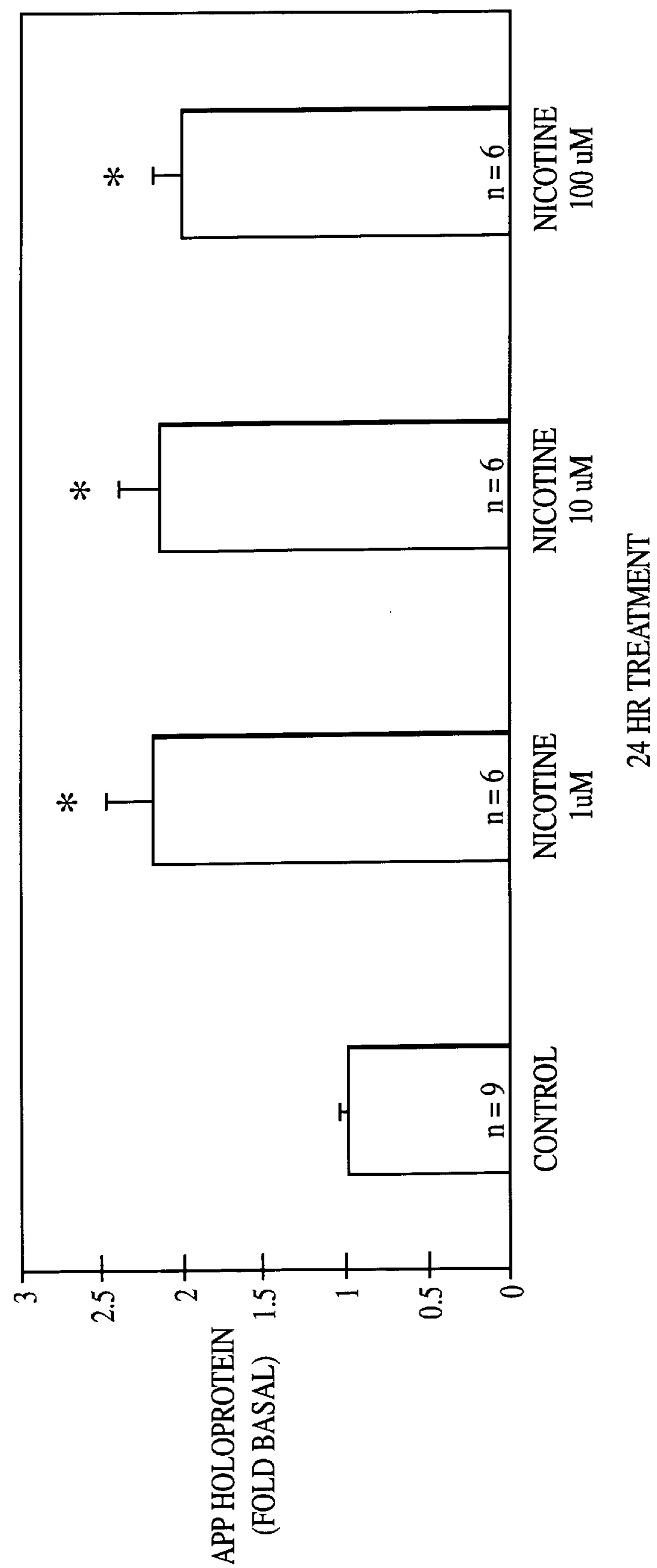
FIGS. 15A, 15B and 15C illustrate the effects of nicotine ditartrate in increasing cellular levels of APP holoprotein, and the effects of EGTA and KN-93 on levels of APP holoprotein stimulated by PG $E_2$.

Treatment of astrocytes for 24 h with 1, 10 or 100 μM nicotine ditartrate significantly increased the amounts of astrocytic APP holoprotein relative to untreated cells (all p<0.05) (FIG. 15A). Similar increases in APP holoprotein (~110–130 kD) were detected by mAb 22C11, antisera R37 or R98 on Western blots.

APP secreted in the media (~110–130 kD) was decreased by 1 h treatment with 1, 10 or 100 μm nicotine ditartrate using mAb 22C11, antiserum R37 or C8 immunodetection (data not shown).

Ion-channel modulator EGTA and calcium/calmodulin kinase inhibitor KN-93 inhibit APP synthesis stimulated by PG $E_2$.

Figure 15B:
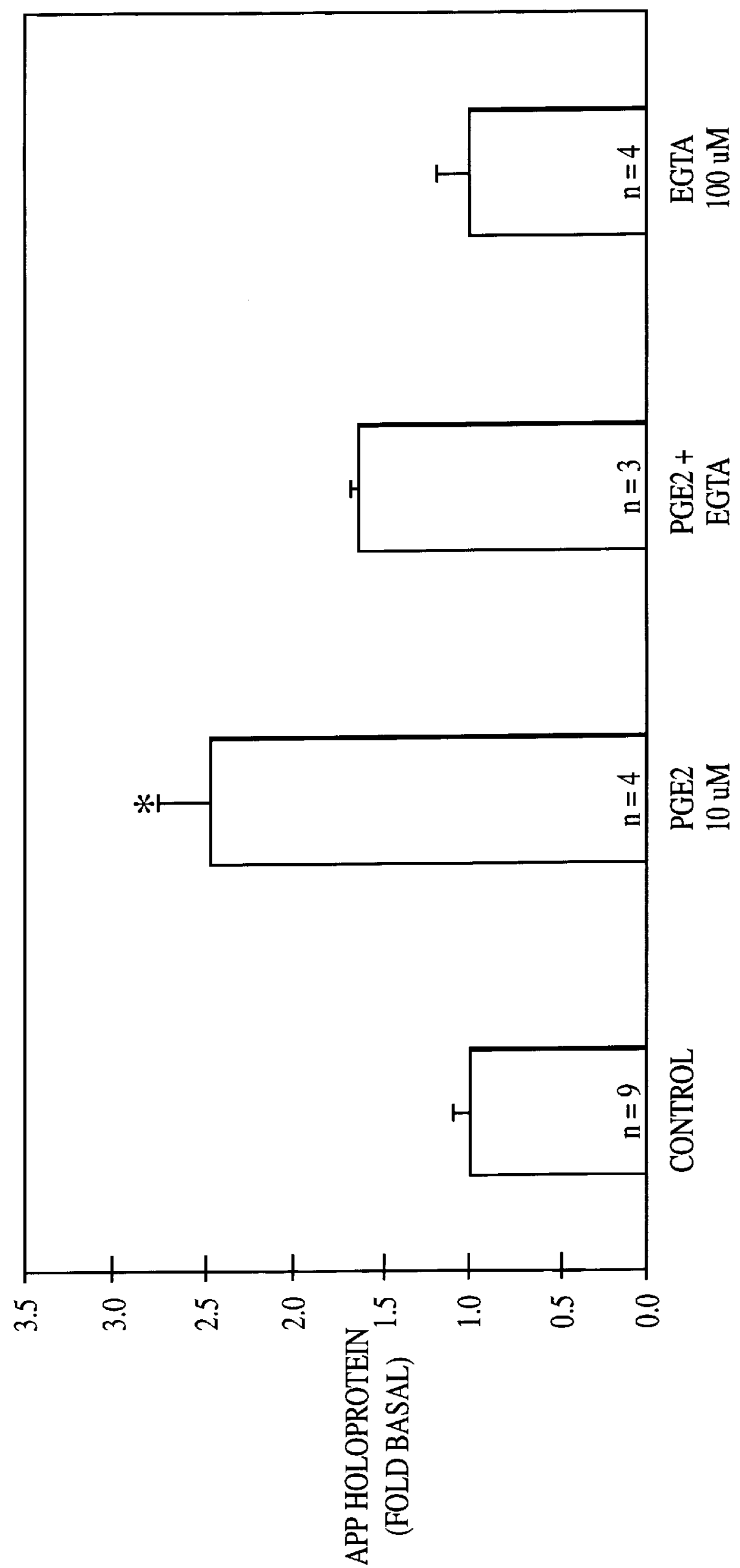
Figure 15C:
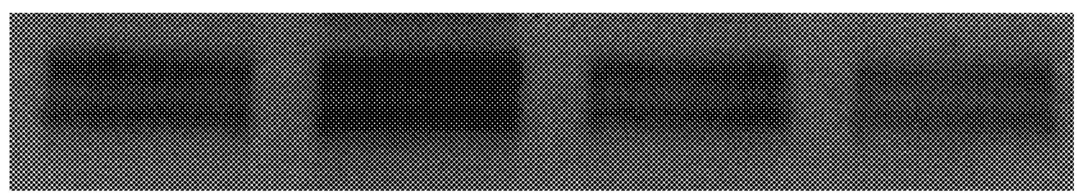

The increases in astrocytic APP holoprotein and mRNA stimulated by 24 h treatments with 10 μm PG $E_2$ were significantly inhibited by co-treatment with either 100 μM EGTA (FIG. 15B) or 100 μM KN-93 {N-[2-[[[3-(4'-chlorophenyl)-2-propenyl]methylamino]methyl]phenyl]-N-(2-hydroxyethyl)-4'-methoxy-benzenesulfonamide phosphate}, available from Research Biochemicals International (FIG. 15C). Representative Northern and Western blots show that the increases in APP mRNA and APP holoprotein, but not the increases in GFAP levels, stimulated by PG $E_2$ (10 μM) are inhibited by EGTA or KN-93 (both 100 μM). Neither EGTA nor KN-93 had a significant effect on cellular cAMP levels stimulated by 10 μM PG $E_2$ (data not shown). Treatment of astrocytes with either EGTA or KN-93 (both 100 μM) alone had no significant effect on basal APP holoprotein or cAMP levels (p>0.05).

8. CONCLUSION

Accordingly, the invention provides compositions and methods for preventing, alleviating, or inhibiting abnormal APP synthesis by the administration of antagonists (e.g., propranolol) of receptors that are coupled to cAMP formation, particularly where the upregulation of such receptors and APP overexpression accompanies brain trauma, neurological disease, or neurodegenerative disorder. The administration of such receptor antagonists suppresses cAMP formation, which in turn inhibits abnormal APP synthesis.

Hence, the invention provides relief from the neuropathological symptoms of diseases, such as Alzheimer's disease, by inhibiting aberrant APP gene expression. It is the overexpression of the APP gene that is believed to cause or strongly contribute to neurodegeneration and cognitive dysfunction in animals and humans.

It should be apparent to those of ordinary skill that the discussion presented herein adequately supports the hypothesis that APP synthesis (as evidenced by increases in mRNA and holoprotein) can be increased by receptors coupled to a different messenger, cAMP formation.

It should also be apparent that other embodiments of the invention can be readily contemplated by those of ordinary skill in the art after reviewing the present specification and teachings. The present invention is not limited, however, to the specific embodiments presented herein and should not be construed so narrowly as to exclude embodiments that fall within the scope and spirit of the invention, which invention is limited solely by the following claims.

What is claimed is:

1. A method of alleviating the negative effects of a neurological disorder or neurodegenerative disease stemming from the aberrant expression, production, or formation of amyloid precursor protein (APP) in a subject comprising administering to a subject suffering from said disorder or disease an effective amount of an antagonist of a β-adrenergic receptor that is coupled to the cellular levels of cAMP.

2. The method of claim 1 in which said antagonist a receptor antagonist of a neurotransmitter, a modulator of signal transduction or ion channels, an immunosuppressant, an anti-inflammatory agent, or combinations thereof, provided that said modulator does not activate protein kinase C.

3. The method of claim 1 in which the administering occurs at least once per day.

4. The method of claim 1 in which the effective amount is between about 0.01 and about 25 mg/kg body weight.

5. The method of claim 4 in which the effective amount is between about 0.1 and about 15 mg/kg body weight.

6. The method of claim 1 in which the effective amount is administered orally, transdermally, topically, parenterally, rectally, opthalmically, or aurally.

7. The method of claim 6 in which the parenteral administration is intramuscular or subcutaneous and the duration of the effect is prolonged by delayed absorption.

8. The method of claim 1 in which the neurological disorder or neurodegenerative disease is Alzheimer's disease, Parkinson's disease, Lou Gehrig's disease, or multiple sclerosis.

9. The method of claim 2 in which the anti-inflammatory agent is a steroidal anti-inflammatory agent, non-steroidal anti-inflammatory agent, salicylate, steroid, receptor site blocker, inhibitor of complement activation, or combinations thereof.

10. The method of claim 2, in which the anti-inflammatory agent is a 5-lipoxygenase inhibitor, phosphodiesterase inhibitor, cyclooxygenase inhibitor, cyclosalicylazosulfapyridine, azulfasalazine, Asacol, Disalcid, Pentesa, Salflex, Trilisate, leukotriene, $B_4$ receptor antagonist, $C_4$ receptor antagonist, $D_4$ receptor antagonist and $E_4$ receptor antagonist, Aerobid, Aristocort, Azmacort, Beclovent, Beconase, Celestone, Cortenema, Cortifoam, Decadron, Delalone, Depo-Medrol, Dexacort, Epifoam, Hydeltra, Hydrocortone, Hydeltrasol, Medrol, Nasacort, Plaquenil, Pediapred, Rhinocort, Solu-Cortef, Vancenase, Vanceril, prostanoid receptor antagonist, prostaglandin receptor antagonist, neurokinin receptor anatagonist, endothelin receptor antagonist, antihistamine, cytokine receptor anatagonist, interleukin receptor anatagonist, or interferon receptor antagonist.

11. The method of claim 2 in which the immunosuppressant is an immunomodulator.

12. The method of claim 11 in which the immunomodulator is Ergamisol, Leukine, Neupogen, cyclophosphamide, colony-stimulating factors, or combinations thereof.

13. The method of claim 2 in which the immunosuppressant is Atgam, Azathioprine, 15-Deoxyspergualine, HypRho, Imuran, Methotrexate, 6-Mercaptopurine, Mycophenolate mefotil, MICRhoGAM, Misoprostol, Methylprednisolone, Orthoclone, Prograf, Rapamycin, ThoGAM, Sandimmune, antithymocyte globulin, antilymphocyte globulin, monoclonal pan-T cell antibody, or combinations thereof.

14. The method of claim 2 in which the ion channel modulator is N-acetylprocainamide HCl, amiloride HCl, 5-(N,N-dimethyl)-amiloride HCl, 5-(N-ethyl-N-isopropyl)-amiloride, 5-(N,N-hexamethylene)-amiloride, 5-(N-methyl-N-isobutyl)-amiloride, 4-aminopyridine, amiodarone HCl, apamin, benzamil HCl, bepridil HCl, β-bungarotoxin, 2,3-butanedione monoxime, calciseptine, charybdotoxin, μ-conotoxin GIIIA, ω-conotoxin GVIA, ω-conotoxin MVIIC, cyclic ADP ribose, cyclopiazonic acid, cyproheptadine HCl, dantrolene sodium salt, dendrotoxin, diltiazem HCl, efaroxan HCl, flunarizine HCl, fluspirilene, glibenclamide, glipizide, 5-hydroxydecanoic acid sodium salt, iberiotoxin, kaliotoxin, lidocaine N-ethyl bromide, loperamide HCl, manoalide, MCD peptide, nicardipine HCl, nifedipine, nifedipine metabolite, (±)-niguldipine HCl, S(+)-niguldipine HCl, R(−)-niguldipine HCl, nimodipine, nitrendipine, 5-nitro-2-(3-phenylpropylamino)benzoic acid, phenamil methanesulfonate, N-phenylanthranylic acid, phentolamine mesylate, pimozide, procainamide HCl, quinidine sulfate, quinine sulfate, ruthenium red, ryanodine, saxitoxin, tetraethylammonium chloride, tetrodotoxin, tetrodotoxin citrate, thapsigargin, tityustoxin-Kα, tolbutamide, triamterene, (±)-verapmil HCl, S(−)-verapmil HCl, R(+)-verapamil HCl, S(−)-methoxyl-verapamil HCl, or R(+)-methoxy-verapamil.

15. The method of claim 2 in which the neurotransmitter antagonist is an antagonist of at least one beta-adrenergic, serotonergic, dopaminergic, adenosine, adrenoreceptors, angiotensin, atrial natriuretic peptide, bombesin, bradykinin, cholecystokinin, gastrin, dopamine, endothelin, GABA, glutamate, interleukin-1, serotonin, leukotriene, vasoactive intestinal polypeptide, pituitary adenylate cyclase activating peptide, prostaglandin $E_2$, histamine, muscarinic acetylcholine, neuropeptide Y, nicotinic acetylcholine, opioid, PAF, prostanoid, purinoceptors, somatostatin, tachykinin, thrombin, vasopressin, oxytocin, VIP, and combinations thereof.

16. A method of alleviating the negative effects of a neurological disorder or neurodegenerative disease stemming from aberrant expression, production, or formation of amyloid precursor protein, in a subject in need thereof, comprising administering a protein kinase A or protein kinase C signaling agent.

17. The method of claim 16 in which the agent is phorbol ester, indolactam, mezerin, diacylglycerol, cAMP, cGMP, related analogs, forskolin, activators of adenylate guanylate cyclase, inhibitors of adenylate guanylate cyclase, modulators of calcium channels, modulators of potassium channels, G-proteins, or combinations thereof.

18. The method of claim 16 in which administration of the signaling agent reduces cyclic AMP levels.

19. A method of stimulating the processing of amyloid precursor protein comprising administering a phorbol ester, a diacylglycerol or a combination thereof, wherein said administration stimulates the processing of amyloid precursor protein.

* * * * *

UNITED STATES PATENT AND TRADEMARK OFFICE

CERTIFICATE OF CORRECTION

PATENT NO. : 6,187,756 B1
APPLICATION NO. : 09/493228
DATED : February 13, 2001
INVENTOR(S) : Lee et al.

It is certified that error appears in the above-identified patent and that said Letters Patent is hereby corrected as shown below:

Col. 1, line 5, insert the following:
-- This invention was made with government support under Grant Number R37 MH028783 awarded by the National Institutes of Health. The government has certain rights in the invention. --

Signed and Sealed this
Twenty-first Day of February, 2012

David J. Kappos
*Director of the United States Patent and Trademark Office*